United States Patent
Tetiker et al.

(10) Patent No.: US 10,303,830 B2
(45) Date of Patent: May 28, 2019

(54) METHODS AND APPARATUSES FOR ETCH PROFILE OPTIMIZATION BY REFLECTANCE SPECTRA MATCHING AND SURFACE KINETIC MODEL OPTIMIZATION

(71) Applicant: Lam Research Corporation, Fremont, CA (US)

(72) Inventors: Mehmet Derya Tetiker, San Francisco, CA (US); Saravanapriyan Sriraman, Fremont, CA (US); Andrew D. Bailey, III, Milpitas, CA (US); Alex Paterson, San Jose, CA (US); Richard A. Gottscho, Pleasanton, CA (US)

(73) Assignee: Lam Research Corporation, Fremont, CA (US)

( * ) Notice: Subject to any disclaimer, the term of this patent is extended or adjusted under 35 U.S.C. 154(b) by 0 days.

(21) Appl. No.: 15/972,063

(22) Filed: May 4, 2018

(65) Prior Publication Data
US 2018/0260509 A1    Sep. 13, 2018

Related U.S. Application Data

(63) Continuation of application No. 15/698,458, filed on Sep. 7, 2017, now Pat. No. 9,996,647, which is a continuation of application No. 15/018,708, filed on Feb. 8, 2016, now Pat. No. 9,792,393.

(51) Int. Cl.
*G06F 17/50*    (2006.01)
*G01B 11/00*    (2006.01)
(Continued)

(52) U.S. Cl.
CPC ........ *G06F 17/5036* (2013.01); *G01B 11/002* (2013.01); *G01N 21/55* (2013.01);
(Continued)

(58) Field of Classification Search
USPC .................................. 716/51, 52, 53, 54, 55
See application file for complete search history.

(56) References Cited

U.S. PATENT DOCUMENTS 5,114,233 A    5/1992    Clark et al.
5,421,934 A    6/1995    Misaka et al.
(Continued)

FOREIGN PATENT DOCUMENTS

WO    WO 2018/204193    11/2018

OTHER PUBLICATIONS

U.S. Office Action, dated Jan. 25, 2018, issued in U.S. Appl. No. 14/972,969.
(Continued)

*Primary Examiner* — Brian Ngo
(74) *Attorney, Agent, or Firm* — Weaver Austin Villeneuve & Sampson LLP

(57) ABSTRACT

Disclosed are methods of optimizing a computer model which relates the etch profile of a feature on a semiconductor substrate to a set of independent input parameters (A), via the use of a plurality of model parameters (B). In some embodiments, the methods may include modifying one or more values of B so as to reduce a metric indicative of the differences between computed reflectance spectra generated from the model and corresponding experimental reflectance spectra with respect to one or more sets of values of A. In some embodiments, calculating the metric may include an operation of projecting the computed and corresponding experimental reflectance spectra onto a reduced-dimensional subspace and calculating the difference between the reflectance spectra as projected onto the subspace. Also disclosed are etch systems implementing such optimized computer models.

29 Claims, 13 Drawing Sheets

(51) Int. Cl.
| | |
|---|---|
| G01N 21/55 | (2014.01) |
| G03F 1/70 | (2012.01) |
| G03F 1/80 | (2012.01) |
| G03F 1/84 | (2012.01) |
| G03F 7/00 | (2006.01) |

(52) U.S. Cl.
CPC ............. *G03F 1/70* (2013.01); *G03F 1/80* (2013.01); *G03F 1/84* (2013.01); *G03F 7/00* (2013.01); *G06F 17/5068* (2013.01); *G01B 2210/56* (2013.01)

(56) References Cited

U.S. PATENT DOCUMENTS

| | | |
|---|---|---|
| 6,268,226 B1 | 7/2001 | Angell et al. |
| 6,410,351 B1 | 6/2002 | Bode et al. |
| 6,650,423 B1 | 11/2003 | Markle et al. |
| 6,684,382 B2 | 1/2004 | Liu |
| 6,753,115 B2 | 6/2004 | Zhang et al. |
| 6,804,572 B1 | 10/2004 | Cooperberg et al. |
| 6,903,826 B2 | 6/2005 | Usui et al. |
| 7,139,632 B2 | 11/2006 | Cooperberg et al. |
| 7,402,257 B1 | 7/2008 | Sonderman et al. |
| 7,504,182 B2 | 3/2009 | Stewart et al. |
| 7,588,946 B2 | 9/2009 | Tso et al. |
| 7,600,212 B2 | 10/2009 | Zach et al. |
| 7,739,651 B2 | 6/2010 | Melvin, III et al. |
| 7,812,966 B2 | 10/2010 | Hoffmann et al. |
| 7,849,423 B1 | 12/2010 | Yenikaya et al. |
| 7,962,867 B2 | 6/2011 | White et al. |
| 8,001,512 B1 | 8/2011 | White |
| 8,279,409 B1 | 10/2012 | Sezginer et al. |
| 8,832,610 B2 | 9/2014 | Ye et al. |
| 9,471,746 B2 | 10/2016 | Rieger et al. |
| 9,547,740 B2 | 1/2017 | Moroz et al. |
| 9,792,393 B2 | 10/2017 | Tetiker et al. |
| 9,996,647 B2 | 6/2018 | Tetiker et al. |
| 10,032,681 B2 | 7/2018 | Bailey, III et al. |
| 10,197,908 B2 | 2/2019 | Sriraman et al. |
| 2003/0008507 A1 | 1/2003 | Bell et al. |
| 2003/0113766 A1 | 6/2003 | Pepper et al. |
| 2004/0019872 A1 | 1/2004 | Lippincott et al. |
| 2005/0074907 A1 | 4/2005 | Kriz et al. |
| 2006/0141484 A1 | 6/2006 | Rucker et al. |
| 2007/0050749 A1 | 3/2007 | Ye et al. |
| 2007/0249071 A1 | 10/2007 | Lian et al. |
| 2007/0281478 A1 | 12/2007 | Ikegami et al. |
| 2008/0035608 A1 | 2/2008 | Thomas et al. |
| 2009/0048813 A1 | 2/2009 | Ichikawa et al. |
| 2009/0087143 A1 | 4/2009 | Jeon et al. |
| 2009/0253222 A1 | 10/2009 | Morisawa et al. |
| 2011/0022215 A1 | 1/2011 | Keil et al. |
| 2011/0292375 A1 | 12/2011 | Marx et al. |
| 2012/0002912 A1 | 1/2012 | Studenkov et al. |
| 2015/0079500 A1 | 3/2015 | Shih et al. |
| 2015/0154145 A1 | 6/2015 | Watanabe et al. |
| 2017/0115556 A1 | 4/2017 | Shim et al. |
| 2017/0147724 A1 | 5/2017 | Regli et al. |
| 2017/0176983 A1 | 6/2017 | Tetiker et al. |
| 2017/0228482 A1 | 8/2017 | Tetiker et al. |
| 2017/0256463 A1 | 9/2017 | Bailey, III et al. |
| 2017/0363950 A1 | 12/2017 | Sriraman et al. |
| 2017/0371991 A1 | 12/2017 | Tetiker et al. |
| 2018/0157161 A1 | 6/2018 | Mailfert et al. |
| 2018/0182632 A1 | 6/2018 | Ye et al. |
| 2018/0314148 A1 | 11/2018 | Tetiker et al. |
| 2019/0049937 A1 | 2/2019 | Tetiker et al. |

OTHER PUBLICATIONS

U.S. Office Action, dated Mar. 22, 2017, issued in U.S. Appl. No. 15/018,708.
U.S. Notice of Allowance, dated Jun. 7, 2017, issued in U.S. Appl. No. 15/018,708.
U.S. Notice of Allowance, dated Feb. 6, 2018 issued in U.S. Appl. No. 15/698,458.
U.S. Office Action, dated Oct. 2, 2017, issued in U.S. Appl. No. 15/698,458.
U.S. Office Action, dated Aug. 10, 2017, issued in U.S. Appl. No. 15/059,073.
Notice of Allowance dated Jan. 11, 2018 issued in U.S. Appl. No. 15/059,073.
U.S. Office Action, dated Dec. 7, 2017, issued in U.S. Appl. No. 15/188,910.
Cooperberg, D.J., et al. (Sep./Oct. 2002) "Semiempirical profile simulation of aluminum etching in a $Cl_2$ / $BCl_3$ plasma," *Journal of Vacuum Science & Technology A.*, 20(5):1536-1556 [doi: http://dx.doi.org/10.1116/1.1494818].
Goodlin et al. (May 2002) "Quantitative Analysis and Comparison of Endpoint Detection Based on Multiple Wavelength Analysis," *201st Meeting of the Electrochemical Society, International Symposium on Plasma Processing XIV*, Abs. 415, Philadelphia, PA, 30 pages.
Hoekstra, R. et al. (Jul./Aug. 1997) "Integrated plasma equipment model for polysilicon etch profiles in an inductively coupled plasma reactor with subwafer and superwafer topography," *Journal of Vacuum Science & Technology A*, 15(4):1913-1921 [doi: http://dx.doi.org/10.1116/1.580659].
Hoekstra, R. et al. (Jul./Aug. 1998) "Microtrenching resulting from specular reflection during chlorine etching of silicon," *Journal of Vacuum Science & Technology B, Nanotechnology and Microelectronics*, 16(4):2102-2104 [doi: http://dx.doi.org/10.1116/1.590135].
Hoekstra, R. et al. (Nov. 1, 1998) "Comparison of two-dimensional and three-dimensional models for profile simulation of poly-Si etching of finite length trenches," *Journal of Vacuum Science & Technology A*, 16(6):3274-3280 [doi:http://dx.doi.org/10.1116/1.581533].
Huard, C.M., et al. (Jan. 17, 2017) "Role of neutral transport in aspect ratio dependent plasma etching of three-dimensional features," *Journal of Vacuum Science & Technology A.*, 35(5):05C301-1-05C301-18. [doi: http://dx.doi.org/10.1116/1.4973953].
Kushner, M.J., (Sep. 18, 2009) "Hybrid modelling of low temperature plasmas for fundamental investigations and equiptment design," *Journal of Physics D.*, 42(1904013):1-20 [doi: 10.1088/0022-3727/42/19/194013].
Lynn et al. (2009) "Virtual Metrology for Plasma Etch using Tool Variables," *IEEE*, pp. 143-148.
Lynn, Shane (Apr. 2011) "Virtual Metrology for Plasma Etch Processes," *A thesis submitted in partial fulfillment for the degree of Doctor of Philosophy in the Faculty of Science and Engineering, Electronic Engineering Department*, National University of Ireland, Maynooth, 361 pages.
Moharam et al. (Jul. 1981) "Rigorous coupled-wave analysis of planar-grating diffraction," *J. Opt. Soc. Am.*, 71(7): 811-818.
Radjenović et al. (2007) "3D Etching profile evolution simulations: Time dependence analysis of the profile charging during SiO2 etching in plasma," *5th EU-Japan Joint Symposium on Plasma Process, Journal of Physics: Conference Series*, 86: 13 pages.
Ringwood et al. (Feb. 2010) "Estimation and Control in Semiconductor Etch: Practice and Possibilities," *IEEE Transactions on Semiconductor Manufacturing*, 23(1):87-98.
Sankaran, A. et al. (Jan. 15, 2005) "Etching of porous and solid $SiO_2$ in Ar/c-$C_4F_8$, $O_2$/c-$C_4F_8$ and Ar/$O_2$/c-$C_4F_8$ plasmas," *Journal of Applied Physics*, 97(2):023307-1-023307-10. [doi: http://dx.doi.org/10.1063/1.1834979] [retrieved on Jan. 29, 2005].
Sankaran, A. et al. (Jul./Aug. 2004) "Integrated feature scale modeling of plasma processing of porous and solid $SiO_2$. I. Fluorocarbon etching," *Journal of Vacuum Science & Technology A.*, 22(4): 1242-1259 [doi: http://dx.doi.org/10.1116/1.1764821].
Yue et al. (Jan./Feb. 2001) "Plasma etching endpoint detection using multiple wavelengths for small open-area wafers," *J. Vac. Sci. Technol. A*, 19(1):66-75.

(56) References Cited

OTHER PUBLICATIONS

Zeng (2012) "Statistical Methods for Enhanced Metrology in Semiconductor/Photovoltaic Manufacturing," A dissertation submitted in partial satisfaction of the requirements for the degree of Doctor of Philosophy in Engineering—Electrical Engineering and Computer Sciences in the Graduate Division of the University of California, Berkeley, 171 pages.
Zhang, D. et al. (Mar./Apr. 2001) "Investigations of surface reactions during $C_2F_6$ plasma etching of $SiO_2$ with equipment and feature scale models," *Journal of Vacuum Science & Technology A*, 19(2):524-538 [doi: http://dx.doi.org/10.1116/1.1349728].
Zhang, Y., (Sep. 30, 2015) Doctoral Dissertation of "Low Temperature Plasma Etching Control through Ion Energy Angular Distribution and 3-Dimensional Profile Simulation," *Dept. of Electrical Engineering at the University of Michigan*, pp. 49-71, Appendix B. pp. 243-248 [doi: http://hdl.handle.net/2027.42/113432].
U.S. Appl. No. 15/367,060, filed Dec. 1, 2016, Mailfert et al.
U.S. Appl. No. 15/583,610, filed May 1, 2017, Tetiker et al.
U.S. Appl. No. 15/673,321, filed Aug. 9, 2017, Tetiker et al.
U.S. Appl. No. 15/946,940, filed Apr. 6, 2018, Feng et al.
U.S. Final Office Action, dated Aug. 27, 2018, issued in U.S. Appl. No. 14/972,969.
U.S. Final Office Action, dated May 23, 2018 issued in U.S. Appl. No. 15/188,910.
U.S. Office Action, dated Jul. 11, 2018 issued in U.S. Appl. No. 15/367,060.
International Search Report and Written Opinion dated Aug. 10, 2018 issued in Application No. PCT/US2018/029874.
U.S. Office Action, dated Jan. 10, 2019, issued in U.S. Appl. No. 14/972,969.
U.S. Notice of Allowance, dated Sep. 27, 2018 issued in U.S. Appl. No. 15/188,910.
U.S. Notice of Allowance, dated Nov. 26, 2018 issued in U.S. Appl. No. 15/367,060.
U.S. Appl. No. 16/224,651, filed Dec. 18, 2018, Sriraman et al.
U.S. Appl. No. 16/260,870, filed Feb. 14, 2019, Bowes et al.

METHODS AND APPARATUSES FOR ETCH PROFILE OPTIMIZATION BY REFLECTANCE SPECTRA MATCHING AND SURFACE KINETIC MODEL OPTIMIZATION

CROSS-REFERENCE TO RELATED APPLICATION

This application is a continuation of U.S. patent application Ser. No. 15/698,458 filed Sep. 7, 2017, by Tetiker et al., entitled "METHODS AND APPARATUSES FOR ETCH PROFILE OPTIMIZATION BY REFLECTANCE SPECTRA MATCHING AND SURFACE KINETIC MODEL OPTIMIZATION, which is a continuation of U.S. patent application Ser. No. 15/018,708 filed on Feb. 8, 2016 (now U.S. Pat. No. 9,792,393), by Tetiker et al., entitled "METHODS AND APPARATUSES FOR ETCH PROFILE OPTIMIZATION BY REFLECTANCE SPECTRA MATCHING AND SURFACE KINETIC MODEL OPTIMIZATION," which applications are incorporated by reference herein in their entirety and for all purposes.

BACKGROUND

The performance of plasma-assisted etch processes is frequently critical to the success of a semiconductor processing workflow. However, optimizing the etch processes can be difficult and time-consuming, oftentimes involving process engineers manually tweaking etch process parameters in an ad hoc fashion in attempt to generate the desired target feature profile. There is currently simply no automated procedure of sufficient accuracy which may be relied upon by process engineers to determine the values of process parameters which will result in a given desired etch profile.

Some models attempt to simulate the physical chemical processes occurring on semiconductor substrate surfaces during etch processes. Examples include the etch profile models of M. Kushner and co-workers as well as the etch profile models of Cooperberg and co-workers. The former are described in Y. Zhang, "Low Temperature Plasma Etching Control through Ion Energy Angular Distribution and 3-Dimensional Profile Simulation," Chapter 3, dissertation, University of Michigan (2015), and the latter in Cooperberg, Vahedi, and Gottscho, "Semiempirical profile simulation of aluminum etching in a $Cl_2/BCl_3$ plasma," J. Vac. Sci. Technol. A 20(5), 1536 (2002), each of which is hereby incorporated by reference in its entirety for all purposes. Additional description of the etch profile models of M. Kushner and co-workers may be found in J. Vac. Sci. Technol. A 15(4), 1913 (1997), J. Vac. Sci. Technol. B 16(4), 2102 (1998), J. Vac. Sci. Technol. A 16(6), 3274 (1998), J. Vac. Sci. Technol. A 19(2), 524 (2001), J. Vac. Sci. Technol. A 22(4), 1242 (2004), J. Appl. Phys. 97, 023307 (2005), each of which is also hereby incorporated by reference in its entirety for all purposes. Despite the extensive work done to develop these models, they do not yet possess the desire degree of accuracy and reliability to find substantial use within the semiconductor processing industry.

SUMMARY

Disclosed are methods of optimizing a computer model which relates the etch profile of a feature on a semiconductor substrate to a set of independent input parameters (A), via the use of a plurality of model parameters (B). The methods may include identifying a set of values for a selected set of the model parameters (B) to be optimized; identifying multiple sets of values for a selected set of independent input parameters (A) to optimize over. Then, for each set of values of A, the methods may further include receiving an experimental reflectance spectra generated from an optical measurement of an experimental etch process performed using the set of values specified of A, and also generating a computed reflectance spectra from the model using the set of values of A and B. In certain such embodiments, the methods may further include modifying one or more values of B and repeating the generation of computed reflectance spectra from the model but now using the modified set of values of B so as to reduce a metric indicative of the differences between the experimental reflectance spectra and corresponding computed reflectance spectra with respect to one or more sets of values of A.

In some embodiments, calculating the metric may include an operation of calculating the differences between the computed and corresponding experimental reflectance spectra and projecting the differences onto a reduced-dimensional subspace, and/or an operation of projecting the computed and corresponding experimental reflectance spectra onto a reduced-dimensional subspace and calculating the difference between the reflectance spectra as projected onto the subspace.

In some embodiments, at least some of the computed reflectance spectra are generated by a process which includes generating a computed etch profile represented by a series of etch profile coordinates using the model, and from the computed etch profile, generating a computed reflectance spectrum by simulating the reflection of electromagnetic radiation off of said computed etch profile.

In some embodiments, the experimental reflectance spectra include reflectance spectra corresponding to a sequence of etch times representing different durations of etch processes, and the computed reflectance spectra include reflectance spectra computed from a model so as to correspond to the same sequence of etch times. In certain such embodiments, the experimental reflectance spectra are generated from optical measurements taken during ongoing etch processes at the sequence of etch times, in some cases, consecutive etch times over at least a portion of the sequence of etch times are separated by 0.01-1 second.

Also disclosed herein are computer models for generating computed etch profiles which have been optimized according to the foregoing methodologies. Also disclosed herein are methods of approximately determining the profile of a feature on a semiconductor substrate after the feature has been etched by an etch process. These methods may include specifying a set of values for a set of independent input parameters corresponding to the etch process, and generating an etch profile using the foregoing optimized computer model with the specified set of values for the independent input parameters. Also disclosed are methods of using the foregoing optimized models to determine a set of values for a set of independent input parameters for an etch process which will approximately yield a desired etch profile of a feature on a semiconductor substrate after the feature is etched by said etch process.

Also disclosed herein are systems for processing semiconductor substrates. These systems may include an etcher apparatus for etching semiconductor substrates whose operation is adjusted by a set of independent input parameters, and a controller for controlling the operation of the etcher apparatus. The controller typically includes a processor and a memory. The memory may store an etched feature profile model optimized by any of the foregoing model optimization methods.

The processor may be configured to use the optimized etched feature profile model stored in the memory to compute an etched feature profile from a set of values for the set of independent input parameters.

These and other features of the disclosure will be presented below with reference to the associated drawings.

BRIEF DESCRIPTION OF THE DRAWINGS

FIG. 4B-1 is a cross section of an idealized feature having parallel lines and illustrating associated dimensions including CD, P, etc.

DETAILED DESCRIPTION

Introduction

Disclosed herein are procedures for improving the practical utility of the etch profile models (EPMs) referred to above (and other similar models) so that they may be used to generate sufficiently accurate representations of semiconductor feature etch profiles, which are good enough approximations to be relied upon in the semiconductor processing industry. Generally, the inventive procedures improve these models' predictive power.

Figure 2:
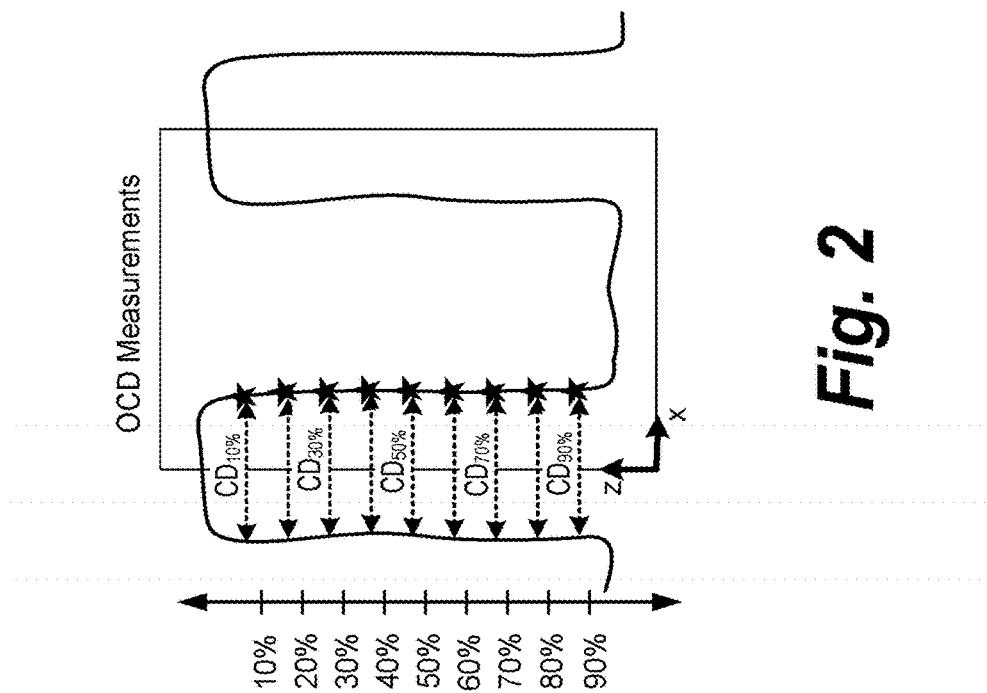
FIG. 2 represents an example of an etch profile, similar to that shown in FIG. 1, but in this figure, computed from experimental measurements made with one or more optical metrology tools.
Figure 1:
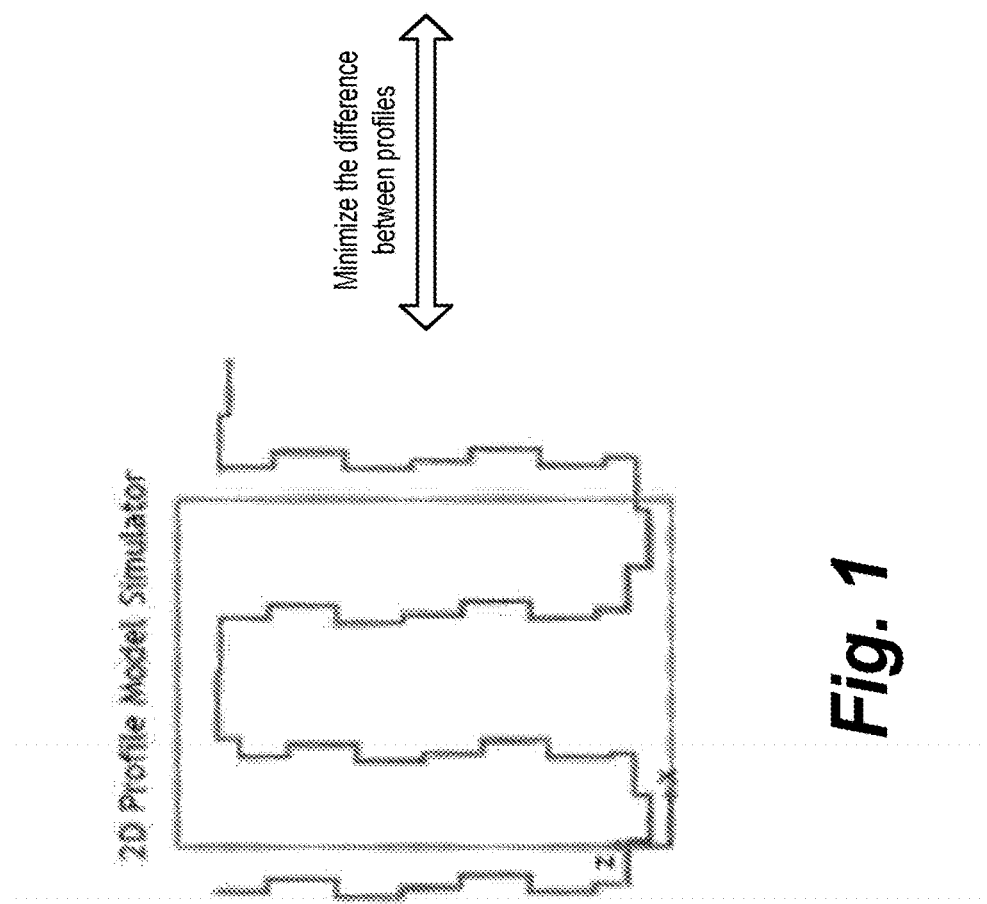
FIG. 1 represents an example of an etch profile as generated computationally from a surface kinetic model of an etch process.

Generally, EPMs and similar models attempt to simulate the etch profile evolution of a substrate feature over time—i.e., the time-dependent changes in the shape of a feature at various spatial locations on the feature's surface—by calculating reaction rates associated with the etch process at each of these spatial locations which result from an incident flux of etchant and deposition species characteristic of the plasma conditions set up in the reaction chamber, and do so over the course of the simulated etch process. The output is a simulated etch profile represented by a discrete set of data points—i.e., profile coordinates—which spatially maps out the shape of the profile. An example of such a simulated etch profile is shown in FIG. 1; the simulated profile may correspond to an actual measured etch profile as shown in FIG. 2. The simulated etch profile's evolution over time depends on the theoretically-modelled, spatially-resolved local etch reaction rates which, of course, depend on the underlying chemistry and physics of the etch process. As such, the etch profile simulation depends on various physical and chemical parameters associated with the chemical reaction mechanisms underlying the etch processes, and also any physical and chemical parameters which may characterize the chamber environment—temperature, pressure, plasma power, reactant flow rate, etc.—which are, generally speaking, under the control of the process engineer.

With respect to the former, the etch profile model thus requires a set of "fundamental" chemical and physical input parameters—examples such as reaction probabilities, sticking coefficients, ion and neutral fluxes, etc.—which are generally not independently controllable and/or even directly knowable by the process engineer, but that nevertheless must be specified as inputs to the simulation. These sets of "fundamental" or "mechanistic" input parameters are thus assumed to have certain values, generally taken from the literature, and their use implicitly invokes certain simplifications of (and approximations to) the underlying physical and chemical mechanisms behind the etch process being modeled.

This disclosure presents procedures that combine experimental techniques and data analysis methodologies to improve the practical industrial applicability of these EPMs of substrate etch processes. Note that the phrase "substrate etch process" includes processes which etch a mask layer or, more generally, processes which etch any layer of material having been deposited on and/or residing on a substrate surface. The techniques focus on the "fundamental" chemical and physical input parameters which are employed by these models and improve the models by using procedures to determine what may be viewed as more effective sets of values for these parameters—effective in the sense that they improve the accuracy of the etch model—even if the optimum values determined for these "fundamental" parameters differ than what the literature (or other experiments) might determine as the "true" physical/chemical values for these parameters.

Figure 3:
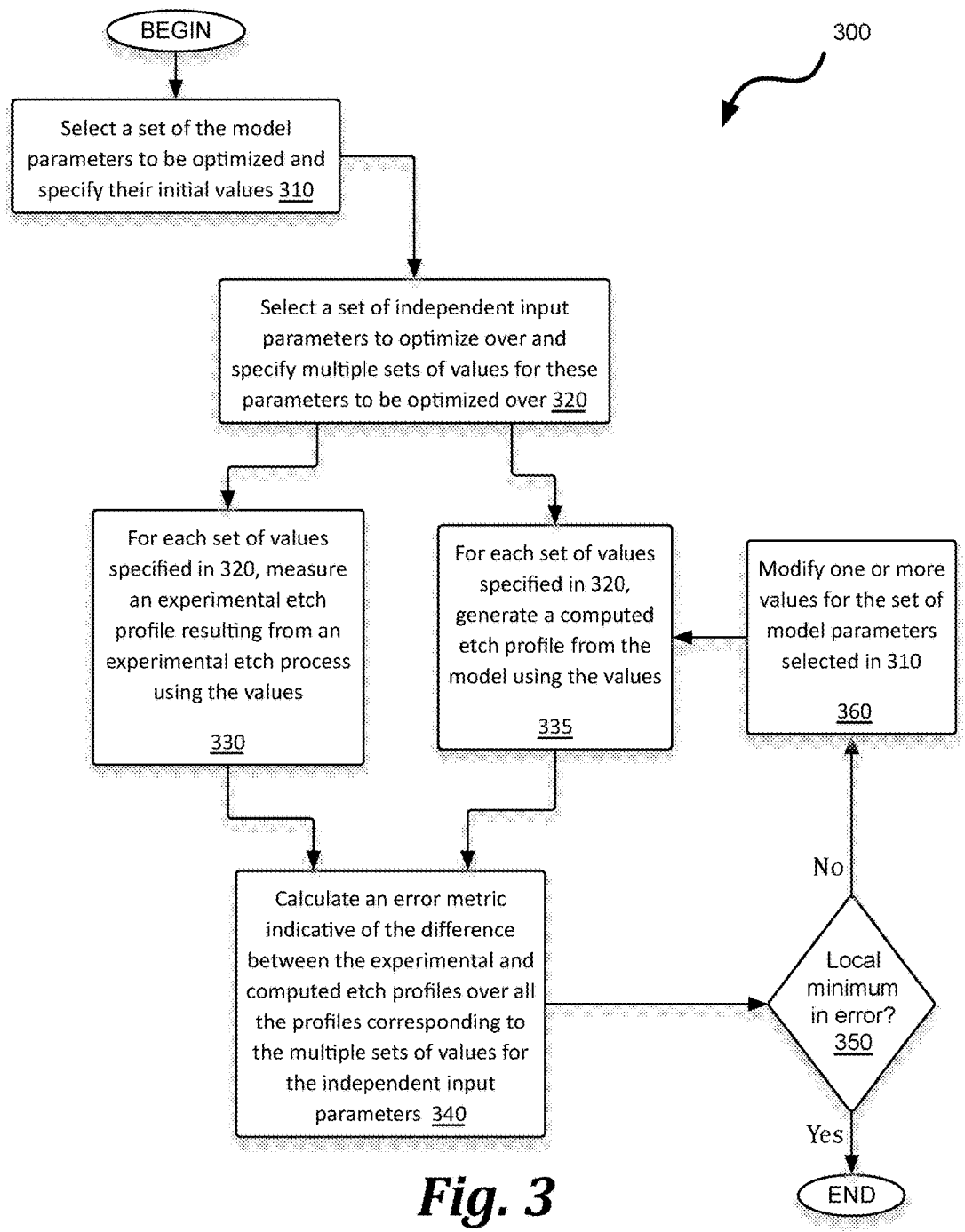
FIG. 3 is a process flow chart representing procedures for optimizing etch profile models with respect to a etch profile coordinate space.

FIGS. 3 and 4, which are discussed more fully below, present flow charts illustrating example processes for generating improved etch profile models. In FIG. 3, for example, the depicted process flow has two input branches, one from experimental measurements and the other from a current version of the model, which version is not yet optimized. Both the experimental branch and the predictive model branch produce etch profile results. These results are compared and the comparison is used to improve the model so that the deviation between the results decreases.

Characterizing etch profile data in detail, in 2 or 3 dimensions as output by an EPM, presents particular challenges for optimizing the model. In various embodiments disclosed herein, the profile data is represented as a series of elevation slices, each having a thickness. In other embodiments, the profile is represented as a series of vectors from a common origin or as a series of geometric forms such as trapezoids. When using many of these elevation slices or other components of the profile, the optimization problem of minimizing the error between experimental and EPM profile, can be computationally demanding. To reduce the required computation, a dimension reduction technique such as principal component analysis is used to identify correlated contributions from the various profile components to the overall physical profile used in the optimization. Presenting the etch profiles in a few principal components or other vectors in a reduced dimensional space can greatly simplify the process of improving the predictive capabilities of the etch profile models. Additionally, such principle components are orthogonal to one another which assures that independent profile contributions can be optimized in isolation.

The following terms are used in the instant specification.

Independent variable—as commonly understood, an independent variable is any variable that causes a response. An etch profile model may include various types of independent variables such as reactor process conditions (e.g., temperature, pressure, gas composition, flow rates, plasma power, and the like), local plasma conditions, and local reaction conditions.

Result variable—as commonly understood, a result variable is a variable that results from the independent variables. Often a result variable is output by a model. In some contexts, a result variable is synonymous with the term dependent variable. In this disclosure an etch profile is a type of result variable.

Input variable—an input variable is similar to an independent variable, but may be more specific in that some independent variables may be fixed for many runs and therefore not technically "input" variables for such runs. In input variable is provided as an input for a run under consideration.

Mechanistic parameter—a mechanistic parameter is a type of independent variable that represents a physical and/or chemical condition at one or more particular locations in a reactor or substrate undergoing etching.

Plasma parameter—a plasma parameter is a type of mechanistic parameter describing local plasma conditions (e.g., plasma density and plasma temperature at particular locations on the substrate).

Reaction parameter—a reaction parameter is a type of mechanistic parameter describing a local chemical or physico-chemical condition.

Process parameter—a process parameter is a reactor parameter over which the process engineer has control (e.g., chamber pressure and pedestal temperature). Process parameters along with substrate characteristics may control values of the mechanistic parameters in an etch reactor.

Model parameter—a model parameter is a type of independent variable that is optimized. It is typically a mechanistic parameter such as a chemical reaction parameter. Initial values of model parameters are unoptimized.

Etch Profiles

Before delving into the details of the etch profile models and the procedures for their improvement, it is useful to describe the concept of a feature's etch profile. Generally, an etch profile (EP) refers to any set of values for a set of one or more geometric coordinates which may be used to characterize the shape of an etched feature on a semiconductor substrate. In a simple case, an etch profile can be approximated as the width of a feature determined halfway to the base of the feature (the midpoint between the feature's base (or bottom) and it's top opening on the surface of the substrate) as viewed through a 2-dimensional vertical cross-sectional slice through the feature. In a more complicated example, an etch profile may be series of feature widths determined at various elevations above the base of the feature as viewed through the same 2-dimensional vertical cross-sectional slice. FIG. 2 provides an illustration of this. Note that, depending on the embodiment, the width may be the distance between one sidewall of the recess feature and the other—i.e. the width of the region which has been etched away—or the width may refer to the width of a column which has been etched on either side. The latter is schematically illustrated in FIG. 2. Note that in some cases, such a width is referred to as a "critical dimension" (labeled "CD" in FIG. 2) and that the elevation from the base of the feature may be referred to as the height or the z-coordinate (labeled as percentages in FIG. 2) of the so-referred-to critical dimension. As mentioned, the etch profile may be represented in other geometric references such as by a group of vectors from a common origin or a stack of shapes such as trapezoids or triangles or a group of characteristic shape parameters that define a typical etch profile such as bow, straight or tapered sidewall, rounded bottom, facet etc.

In this way, a series of geometric coordinates (e.g., feature widths at different elevations) maps out a discretized portrayal of a feature's profile. Note, that there are many ways to express a series of coordinates which represent feature width at different elevations. For instance, each coordinate might have a value which represents a fractional deviation from some baseline feature width (such as an average feature width, or a vertically averaged feature width), or each coordinate might represent the change from the vertically adjacent coordinate, etc. In any event, what is being referred to as "width" and, generally, the scheme being used for the set of profile coordinates used to represent an etch profile will be clear from the context and usage. The idea is that a set of coordinates are used represent the shape of the feature's etched profile. It is also noted that a series of geometric coordinates could also be used to describe the full 3-dimensional shape of a feature's etched profile or other geometric characteristic, such as the shape of an etched cylinder or trench on a substrate surface. Thus, in some embodiments, a etch profile model may provide a full 3-D etch shape of the feature being modeled.

Etch Profile Models

The etch profile models (EPMs) compute a theoretically determined etch profile from a set of input etch reaction parameters (independent variables) characterizing the underlying physical and chemical etch processes and reaction mechanisms. These processes are modelled as a function of time and location in a grid representing features being etched and their surroundings. Examples of input parameters include plasma parameters such as ion flux and chemical reaction parameters such as the probability that a particular chemical reaction will occur. These parameters (and particularly, in some embodiments, the plasma parameters) may be obtained from various sources, including other models which calculate them from general reactor configurations and process conditions such as pressure, substrate temperature, plasma source parameters (e.g., power, frequencies, duty cycles provided to the plasma source), reactants, and their flow rates. In some embodiments, such models may be part of the EPM.

As explained, EPMs take reaction parameters as independent variables and functionally generate etch profiles as response variables. In other words, a set of independent variables are the physical/chemical process parameters used as inputs to the model, and response variables are the etch profile features calculated by the model. The EPMs employ one or more relationships between the reaction parameters and the etch profile. The relationships may include, e.g., coefficients, weightings, and/or other model parameters (as well as linear functions of, second and higher order polynomial functions of, etc. the reaction parameters and/or other model parameters) that are applied to the independent variables in a defined manner to generate the response variables, which are related to the etch profiles. Such weightings, coefficients, etc. may represent one or more of the reaction parameters described above. These model parameters are tuned or adjusted during the optimization techniques described herein. In some embodiments, some of the reaction parameters are model parameters to be optimized, while others are used as independent input variables. For example, chemical reaction parameters may be optimizable model parameters, while plasma parameters may be independent variables.

In general, a "response variable" represents an output and/or effect, and/or is tested to see if it is the effect. An "independent variable" represents an inputs and/or causes, and/or is tested to see if it is the cause. Thus, a response variable may be studied to see if and how much it varies as the independent variables vary. An independent variable may also be known as a "predictor variable," "regressor," "controlled variable," "manipulated variable," "explanatory variable," or "input variable."

As explained, some EPMs employ input variables (a type of independent variables) that may be characterized as fundamental reaction mechanistic parameters and may be viewed as fundamental to the underlying chemistry and physics and therefore the experimental process engineer generally does not have control over these quantities. In the etch profile model, these variables are applied at each location of a grid and at multiple times, separated by defined time steps. In some implementations, the grid resolution may vary between about a few Angstroms and about a micrometer. In some implementations, the time steps may vary between about 1e-15 and 1e-10 seconds. In certain embodiments, the optimization employs two types of mechanistic independent variables: (1) local plasma parameters, and, and (2) local chemical reaction parameters. These parameters are "local" in the sense that they may vary a function of position, in some cases down to the resolution of the grid. Examples of the plasma parameters include local plasma properties such as fluxes and energies of particles such ions, radicals, photons, electrons, excited species, depositor species and their energy and angular distributions etc. Examples of chemical and physico-chemical reaction parameters include rate constants (e.g., probabilities that a particular chemical reaction will occur at a particular time), sticking coefficients, energy threshold for etch, reference energy, exponent of energy to define sputter yields, angular yield functions and its parameters, etc. Further, the parameterized chemical reactions include reactions in which the reactants include the material being etched and an etchant. It should be understood that the chemical reaction parameters may include various types of reactions in addition to the reactions that directly etch the substrate. Examples of such reactions include side reactions, including parasitic reactions, deposition reactions, reactions of by-products, etc. Any of these might affect the overall etch rate. It should also be understood that the model may require other input parameters, in addition to the above-mentioned plasma and chemical reaction input parameters. Examples of such other parameters include the temperature at the reaction sites, the partial pressure or reactants, etc. In some cases, these and/or other non-mechanistic parameters may be input in a module that outputs some of the mechanistic parameters.

In some embodiments, initial (unoptimized) values for the EPM model variables, as well as independent variables that are fixed during optimization (e.g., the plasma parameters in some embodiments) may be obtained from various sources such as the literature, calculations by other computational modules or models, etc. In some embodiments, the independent input variables—such as the plasma parameters—may be determined by using a model such as, for the case of the plasma parameters, from an etch chamber plasma model. Such models may calculate the applicable input EPM parameters from various process parameters over which the process engineer does have control (e.g., by turning a knob)—e.g., chamber environment parameters such as pressure, flow rate, plasma power, wafer temperature, ICP coil currents, bias voltages/power, pulsing frequency, pulse duty cycle, and the like.

When running an EPM, some of the independent variables are set to known or expected parameter values used to perform the experiments. For example, the plasma parameters may be fixed to known or expected values at locations in modeled domain. Other independent variables—described herein as parameters of the model or the model parameters—are those which are selected to be tuned by the optimization procedure described below. For example, the chemical reaction parameters may be the tuned model parameters. Thus, in a series of runs corresponding to a given measured experimental etch profile, the model parameters are varied in order to elucidate how to choose values of these parameters to best optimize the model.

EPMs may take any of many different forms. Ultimately, they provide a relationship between the independent and response variables. The relationship may be linear or non-linear. Generally, an EPM is what is referred to in the art as a cell-based Monte Carlo surface reaction model. These models, in there various forms, operate to simulate a wafer feature's topographical evolution over time in the context of semiconductor wafer fabrication. The models launch pseudo-particles with energy and angular distributions produced by a plasma model or experimental diagnostics for arbitrary radial locations on the wafer. The pseudo-particles are statistically weighted to represent the fluxes of radicals and ions to the surface. The models address various surface reaction mechanisms resulting in etching, sputtering, mixing, and deposition on the surface to predict profile evolution. During a Monte Carlo integration, the trajectories of various ion and neutral pseudo-particles are tracked within a wafer feature until they either react or leave the computational domain. The EPM has advanced capabilities for predicting etching, stripping, atomic layer etching, ionized metal physical vapor deposition, and plasma enhanced chemical vapor deposition on various materials. In some embodiments, an EPM utilizes a rectilinear mesh in two or three dimensions, the mesh having a fine enough resolution to adequately address/model the dimensions of the wafer feature (although, in principle, the mesh (whether 2D or 3D) could utilize non-rectilinear coordinates as well). The mesh may be viewed as an array of grid-points in two or three dimensions. It may also be viewed as an array of cells which represent the local area in 2D, or volume in 3D, associated with (centered at) each grid-point. Each cell within the mesh may represent a different solid material or a mixture of materials. Whether a 2D or 3D mesh is chosen as a basis for the modeling may depend on the class/type of wafer feature being modelled. For instance, a 2D mesh may be used to model a long trench feature (e.g., in a polysilicon substrate), the 2D mesh delineating the trench's cross-sectional shape under the assumption that the geometry of the ends of the trench are not too relevant to the reactive processes taking place down the majority of the trench's length away from its ends (i.e., for purposes of this cross-sectional 2D model, the trench is assumed infinite, again a reasonable assumption for a trench feature away from its ends). On the other hand, it may be appropriate to model a circular via feature (a through-silicon via (TSV)) using a 3D mesh (since the x,y horizontal dimensions of the feature are on par with each other).

Mesh spacing may range from sub-nanometer (e.g., from 1 Angstrom) up to several micrometers (e.g., 10 micrometers). Generally, each mesh cell is assigned a material identity, for example, photoresists, polysilicon, plasma (e.g., in the spatial region not occupied by the feature), which may change during the profile evolution. Solid phase species are represented by the identity of the computational cell; gas phase species are represented by computational pseudo-particles. In this manner, the mesh provides a reasonably detailed representation (e.g., for computational purposes) of the wafer feature and surrounding gas environment (e.g., plasma) as the geometry/topology of the wafer feature evolves over time in a reactive etch process.

Etch Experiments and Profile Measurements

To train and optimize the EPMs presented in the previous section, various experiments may be performed in order to determine—as accurately as the experiments allow—the actual etch profiles which result from actual etch processes performed under the various process conditions as specified by various sets of etch process parameters. Thus, for instance, one specifies a first set of values for a set of etch process parameters—such as etchant flow rate, plasma power, temperature, pressure, etc.—sets up the etch chamber apparatus accordingly, flows etchant into the chamber, strikes the plasma, etc., and proceeds with the etching of the first semiconductor substrate to generate a first etch profile. One then specifies a second set of values for the same set of etch process parameters, etches a second substrate to generate a second etch profile, and so forth.

Various combinations of process parameters may be used to present a broad or focused process space, as appropriate, to train the EPM. The same combinations of process parameters are then used to calculate (independent) input parameters, such as the mechanistic parameters, to the EPM to provide etch profile outputs (response variables) that can be compared against the experimental results. Because experimentation can be costly and time consuming, techniques can be employed to design experiments in a way that reduces the number of experiments that need be conducted to provide a robust training set for optimizing the EPM. Techniques such as design of experiments (DOE) may be employed for this purpose. Generally, such techniques determine which sets of process parameters to use in various experiments. They choose the combinations of process parameters by considering statistical interactions between process parameters, randomization, and the like. As an example, DOE may identify a small number of experiments covering a limited range of parameters around the center point of a process that has been finalized.

Typically, a researcher will conduct all experiments early in the model optimization process and use only those experiments in the optimization routine iterations until convergence. Alternatively, an experiment designer may conduct some experiments for early iterations of the optimization and additional experiments later as the optimization proceeds. The optimization process may inform the experiment designer of particular parameters to be evaluated and hence particular experiments to be run for later iterations.

One or more in-situ or offline metrology tools may be used to measure the experimental etch profiles which result from these experimental etch process operations. Measurements made be made at the end of the etch processes, during the etch processes, or at one or more times during the etch processes. When measurements are made at the end of an etch process, the measurement methodology may be destructive, when made at intervals during the etch process, the measurement methodology would generally be non-destructive (so not to disrupt the etch). Examples of appropriate metrology techniques include, but not limited to, LSR, OCD, and cross-sectional SEM. Note that a metrology tool may directly measure a feature's profile, such as is the case of SEM (wherein the experiment basically images a feature's etch profile), or it may indirectly determine a feature's etch profile, such as in the case of OCD measurements (where some post-processing is done to back-out the feature's etch profile from the actual measured data).

In any event, the result of the etch experiments and metrology procedures is a set of measured etch profiles, each generally including a series of values for a series of coordinates or a set of grid values which represent the shape of the feature's profile as described above. An example is shown in FIG. 2. The etch profiles may then be used as inputs to train, optimize, and improve the computerized etch profile models as described below.

Model Parameter Tuning/Optimization

Each measured experimental etch profile provides a benchmark for tuning the computerized etch profile model. Accordingly, a series of calculations are performed with the etch profile model by applying the experimental etch profiles to see how the model deviates from reality in its prediction of etch profiles. With this information, the model may be improved.

FIG. 3 presents a flowchart illustrating a set of operations 300 for tuning and/or optimizing an etch profile model, such as those described above. In some embodiments, such a tuned and/or optimized model reduces—and in some cases substantially minimizes—a metric which is related to (indicative of, quantifies, etc.) the combined differences between the etch profiles which are measured as a result of performing the etch experiments, and the corresponding computed etch profiles as generated from the model. In other words, an improved model may reduce the combined error over the different experimental process conditions (as designated by the different sets of specified values of the selected process parameters—which are used to compute independent input parameters to the EPM).

As shown in FIG. 3, the optimization procedure 300 begins at operation 310 with the selection of a set of model parameters to be optimized. Again, these model parameters may be chosen to be parameters which characterize the underlying chemical and physical processes over which the process engineer has no control. Some or all of these will be adjusted based on the experimental data to improve the model. In some embodiments, these model parameters may be reaction parameters and include reaction probabilities and/or (thermal) rate constants, reactant sticking coefficients, etch threshold energies for physical or chemical sputtering, exponent dependence on energy, etch angular yield dependencies and parameters associated with the angular yield curve, etc. Note that, in general, the optimization is done with respect to a particular given/specified mixture of chemical species flowed into the etch chamber (though it should be understood that the chemical composition of the etch chamber will change as the etch process proceeds). In some embodiments, the reaction parameters are fed into the EPM in a separate input file from the other input parameters (such as the plasma parameters).

In some embodiments, the model parameters may include the specification of which particular chemical reactions are to be modelled by the etch process. One of ordinary skill in the art will appreciate that, for a given etch process, there may be many ongoing reactions occurring in the etch chamber at any time. These include the main etch reaction itself, but it may also include side reactions of the main etch process, and reactions involving by-products of the main etch reaction, reactions between by-products, reactions involving by-products of by-products, etc. Thus, in some embodiments, selection of the model parameters involves choosing which reactions to include in the model. Presumably, the more reactions that are included, the more accurate the model, and the more accurate the corresponding computed etch profile. However, increasing the complexity of the model by including more reactions, increases the computational cost of the simulation. It also results in there being more reaction parameters to optimize. This may be good if the particular reaction which is added is important to the overall etch kinetics. However, if the additional reaction is not critical, the addition of another set of reaction parameters may make the optimization procedure more difficult to converge. Once again, the choices of which reactions to include and the rate constants or reaction probabilities associated with these reactions may be fed into the EPM in their own input file (e.g., separate from the plasma parameters). In certain embodiments, for a given set of reactant species, the probabilities of the various alternative/competing reaction pathways for each species should sum to unity. And, once again, it should be appreciated that the specification of reactions to include, reaction probabilities, etc. (e.g., in the input file) would generally be done for a given/specified mixture of chemical species which are being flowed into the etch chamber to perform the etch process/reaction (and the optimization would generally be with respect to this given mixture, though in some embodiments, one can see that what is learned with respect to one chemical mixture, may have applicability to similar/related chemical mixtures).

In any event, to begin the optimization process shown in the flowchart of FIG. 3, initial values generally must be chosen for the various model parameters being optimized (such as the reaction probabilities, sticking coefficients, etc.). This is done in operation 310. The initial values may be those found in the literature, those calculated based on other simulations, determined from experiment, or known from previous optimization procedures, etc.

The model parameters chosen and initialized in operation 310 are optimized over a set of independent input parameters which are given multiple sets of values in operation 320. Such independent input parameters may include parameters which characterize the plasma in the reaction chamber. In some embodiments, these plasma parameters are fed into the EPM via an input file which is separate from the input file used for the reaction parameters (just described). The multiple sets of values for the independent input parameters (e.g., plasma parameters) thus specify different points in the space of the selected independent input parameters. For example, if the input parameters chosen to be optimized over are temperature, etchant flux, and plasma density, and 5 sets of values are chosen for these selected input parameters, then one has identified 5 unique points in the selected 3-dimensional input parameter space of temperature, etchant flux, and plasma density—each of the 5 points in the space corresponding to a different combination of temperature, etchant flux, and plasma density. As mentioned, an experimental design procedure such as DOE may be employed to select the sets of input parameters.

Once chosen, for each combination of input parameters, in operation 330 an etch experiment is performed in order to measure an experimental etch profile. (In some embodiments, multiple etch experiments are performed for the same combination of values for the input parameters and the resulting etch profile measurements averaged together (possibly after discarding outliers, etc.), for example.) This set of benchmarks is then used for tuning and optimizing the model as follows: In operation 335 an etch profile is computed for each combination of values of the input parameters, and in operation 340 an error metric is calculated which is indicative of (related to, quantifies, etc.) the difference between the experimental and computed etch profiles over all the different sets of values for the input parameters.

Note that this set of computed etch profiles (from which the error metric is calculated) corresponds to a set of previously chosen model parameters as specified in operation 310. A goal of the optimization procedure is to determine more effective choices for these model parameters. Thus, in operation 350 it is determined whether the currently specified model parameters are such that the error metric calculated in operation 340 is locally minimized (in terms of the space of model parameters), and if not, one or more values of the set of model parameters are modified in operation 360, and then used to generate a new set of etch profiles—repeating operation 335 as schematically indicated in FIG. 3's flowchart—and thereafter a new error metric is calculated in a repeating of operation 340. The process then proceeds again to operation 350 where it is determined whether this new combination of model parameters represents a local minimum over all the sets of input parameters as assessed by the error metric. If so, the optimization procedure concludes, as indicated in the figure. If not, the model parameters are again modified in operation 360 and the cycle repeats.

Figure 4A:
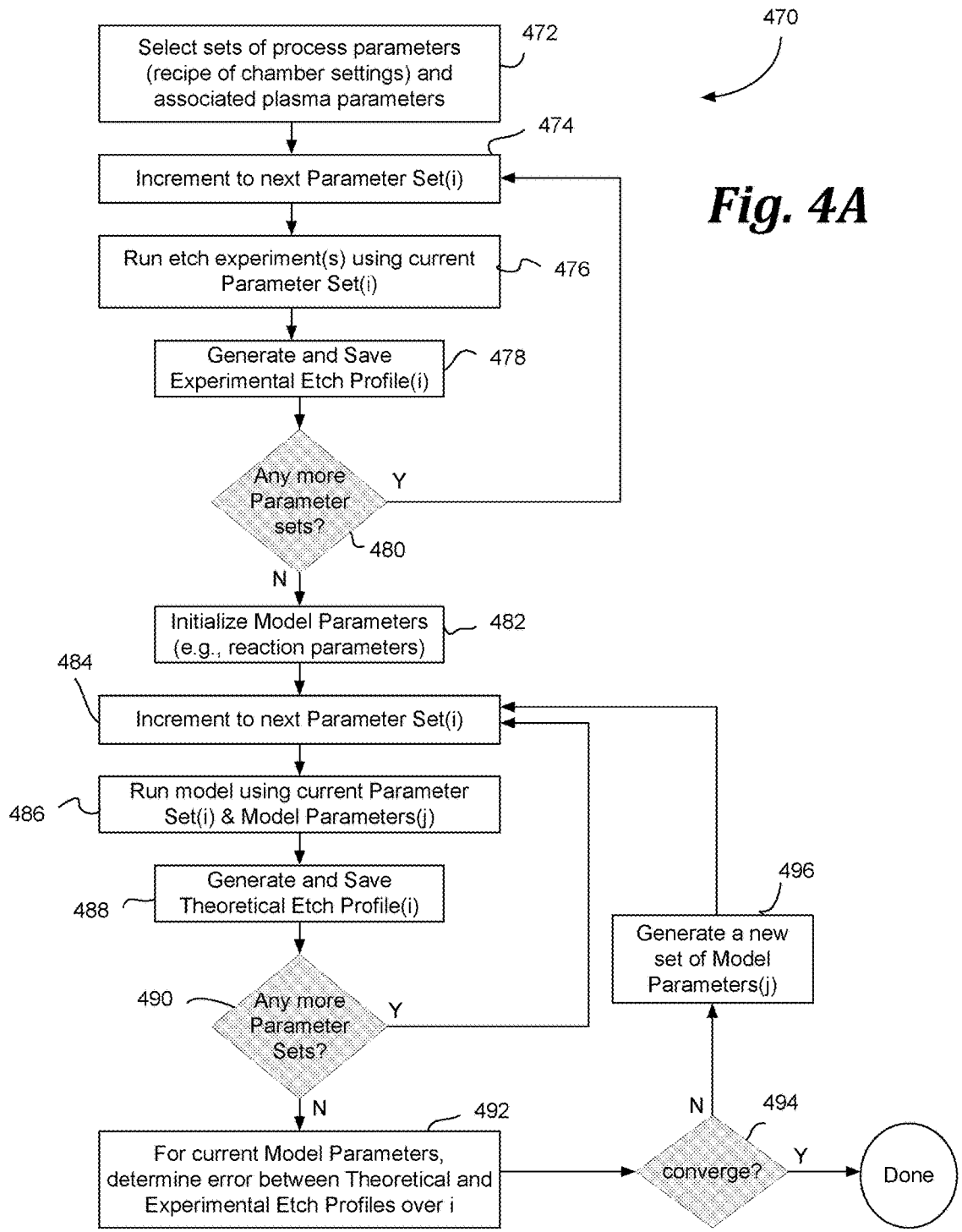
FIG. 4A is a process flow chart representing procedures for optimizing etch profile models, and particularly certain model parameters used in such models.

FIG. 4A presents a flowchart of a method 470 for refining model parameters in an etch profile model. As depicted, method 470 begins by collecting experimental etch profiles generated for a controlled series of etch chamber parameter sets. At a later stage, the method compares these experimentally generated etch profiles to theoretically generated etch profiles produced using the etch profile model. By comparing the experimentally and theoretically generated etch profiles, a set of model parameters used by the etch profile model can be refined to improve the model's ability to predict etch profiles.

In the depicted method, the process begins with an operation 472 where sets of process parameters are selected for use in both the computational and experimental stages. These process parameters define a range of conditions over which the comparison is conducted. Each set of process parameters represents a collection of settings for operating the etch chamber. As mentioned, examples of process parameters include chamber pressure, pedestal temperature, and other parameters that can be selected and/or measured within the etch chamber. Alternatively, or in addition, each set of process parameters represents a condition of work piece being etched (e.g., line width and line pitch formed through etching).

After selecting the sets of process parameters for the experimental runs (note that a set of independent input parameters for the EPM optimization will correspond to (and/or be computed from) each set of process parameters), the experiments begin. This is depicted by a loop over multiple parameter sets and includes operations 474, 476, 478, and 480. Operation 474 simply represents incrementing to the next process parameter set (Parameter Set(i)) for running a new experiment. Once the parameter set is updated, the method runs a new etch experiment (block 476) using the parameters of the current parameter set. Next, the method generates and saves an experimental etch profile (block 478) measured on the work piece after the etch experiment runs with the current parameter set. The "generate and save etch profile" operation provides the etch profile in a reduced dimensional space, as explained above, such as a principal components representation of the etch profile.

Each time a new process parameter set is used in an experiment, the method determines whether there are any more parameter sets to consider, as illustrated at decision block 480. If there are additional parameter sets, the next parameter set is initiated as illustrated at block 474. Ultimately, after all the initially defined process parameter sets are considered, decision block 480 determines that there are no more to consider. At this point, the process is handed off to the model optimization portion of the process flow.

Initially in the model optimization portion of the flow, a set of model parameters (Model Parameters(j)) is initiated as illustrated at block 482. As explained, these model parameters are parameters that the model uses to predict etch profiles. In the context of this process flow, these model parameters are modified to improve the predictive ability of the EPM. In some embodiments, the model parameters are reaction parameters representing one or more reactions to take place in the etch chamber. In one example, the model parameters are reaction rate constants or the probabilities that a particular reactions will take place. Also, as explained elsewhere herein, the etch profile model may employ other parameters that remain fixed during the optimization routine. Examples of such parameters include physical parameters such as plasma conditions.

After the model parameters are initialized at operation 482, the method enters an optimization loop where it generates theoretical etch profiles corresponding to each of the process parameter sets used to generate the experimental etch profiles in the experimental loop. In other words, the method uses the EPM to predict etch profiles which correspond to each of the process parameter sets (i.e., for all the different Parameter Set(i)'s). Note, however, that for each of these process parameter sets, what is actually input into the EPM (to run it) is a set of independent input parameters which correspond to the given process parameters. For some parameters, an independent input parameter may be the same as a process parameter; but for some parameters, the independent input parameter (actually fed into the EPM) may be derived/calculated from the physical process parameter; thus they correspond to one another, but they may not be the same. It should therefore be understood that in the context of this optimization loop in FIG. 4A (operations 482-496), the EPM is—to be very precise about it—run with respect to a set of independent input parameters corresponding to "Parameter Set(i)", whereas in the experimental loop (operations 472-480) the experiments are run with process parameters corresponding to "Parameter Set(i)."

In any event, initially in this loop, the method increments to a next one of the parameter sets that were initially set in operation 472. See block 484. With this selected parameter set, the method runs the etch profile model using the current set of model parameters. See block 486. Thereafter, the method generates and saves the theoretical etch profile for the current combination of a parameter set and model parameters (Parameter Set(i) and Model Parameter(j)). See block 488. The "generate and save etch profile" operation provides the etch profile in a reduced dimensional space such as a principal components representation of the etch profile.

Ultimately all the parameter sets are considered in this loop. Before that point, a decision block 490 determines that additional parameter sets remain and returns control to block 484 where the parameter set is incremented to the next parameter set. The process of running the model and generating and saving theoretical etch profiles repeats for each of the parameter sets (Parameter Set(i)).

When there are no remaining parameter sets to consider for the model parameters currently under consideration (Model Parameters(j)), the process exits this loop and calculates an error between the theoretical etch profile and the experimental etch profiles. See block 492. In certain embodiments, the error is determined across all the Parameter Sets(i) for the process parameters, not just one of them.

The method uses the error determined in block 492 to decide whether the optimization routine for the model parameters has converged. See block 494. As described below, various convergence criteria can be used. Assuming that the optimization routine has not converged, process control is directed to a block 496 where the method generates a new set of model parameters (Model Parameter(j)) which could improve the model's predictive ability. With the new set of model parameters, process control returns to the loop defined by blocks 484, 486, 488, and 490. While in this loop, the Parameter Set(i) is incremented repeatedly and each time the model runs to generate a new theoretical etch profile. After all parameter sets are considered, the error between the theoretical and experimental etch profiles is again determined at block 492 and the convergence criteria and is again applied at block 494. Assuming that the convergence criterion is not yet met, the method generates yet another set of model parameters for testing in the manner just described. Ultimately, a set of model parameters is chosen that meets the convergence criterion. The process is then completed. In other words, the method depicted in FIG. 4 has produced a set of model parameters that improve the predictive ability of the etch profile model.

Figure 4B:
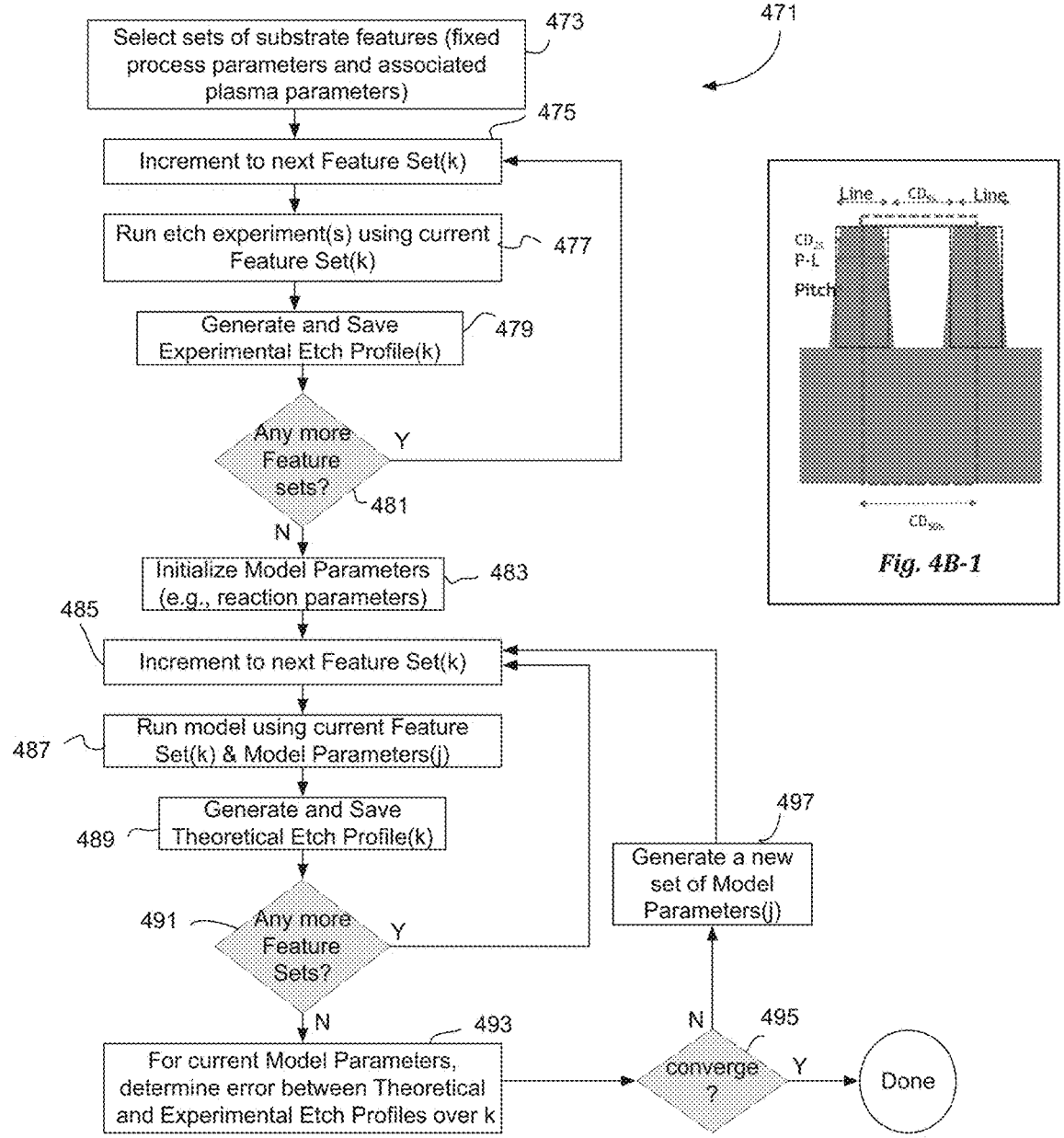
FIG. 4B is a process flow chart representing procedures for optimizing etch profile models, and particularly certain model parameters used in such models.

A related procedure is depicted in FIG. 4B. As shown there, the experimental and theoretical etch profiles are generated for different substrate feature structures, rather than different process conditions. Otherwise the basic process flow is the same. In some implementations, both feature structures and process conditions are varied for the experimental and theoretical operations.

The different features may include different "line" and "pitch" geometries. See FIG. 4B-1. Pitch refers to smallest unit cell width that covers the feature being etched that will be repeated many times. Line refers to the total thickness between two adjacent sidewalls, assuming symmetry. As an example, the method may run repeating geometries of L50P100, L100P200, L100P300, L75 P150 etc. where numbers represent the line width and pitch in nanometers.

In the depicted embodiment, a process 471 begins by selecting fixed and varying parameters (model parameters) of the etch profile model. These may be physical and chemical reaction parameters in some embodiments. Additionally, the substrate features are selected. See operation 473.

For each feature geometry (incremented Feature Set(k) as illustrated in operations 475 and 481), the method runs the etch process for using the current feature geometry, generates the experimental etch profile (Experimental Etch Profile (k)), and saves the etch profile. See operations 477 and 479. As before, each experimental etch profile is saved in a reduced dimensional representation.

Thereafter, the method initializes the model parameters (Model Parameters(j)) for tuning. See operation 483. For each feature geometry (incremented as Feature Set(k) in operations 485 and 491), the method runs the etch profile model generates a theoretical etch profile (Theoretical Etch Profile(k)), and saves the etch profile. See operations 487 and 489. As before, each theoretical etch profile is saved in a reduced dimensional representation.

For each set of Model Parameters(j) considered in the loop containing operations 487 and 489, the method compare s the theoretical and experimental etch profiles to determine the error between the etch profiles over all the substrate features sets. See operation 493. If the process has converged, as determined at operation 495, the process is complete and the current model parameters are selected. If the process has not converged, the method generates a new set of Model Parameters(j) and returns again to the loop defined by operations 485, 487, 489, and 491.

In some embodiments, a separate model parameter set is selected for each feature set. In such cases, the method may plot or otherwise determine a relationship between line/pitch ratio (or another characteristics of the features) and the final converged model parameters. If the converged model parameter values are reasonably constant, possibly with some noise, the method use the average model parameter values for the improved etch profile model. If the converged model parameter values exhibit a trend, the method may use polynomial fit do develop a function that may be used to select model parameter values for each feature set (e.g., line and pitch geometry).

As should be apparent, feature sets, process parameter sets, or other variables are used to conduct multiple experiments and therefore produce multiple experimentally-determined etch profiles. In some implementations, half or some other fraction of these etch profiles (and associated parameter sets) are used for training, as illustrated in the above flow charts, and the remaining etch profiles are used for validation. The training etch profiles generate tuned model parameters, which are used in the etch profile model and validated by applying the tuned model to predict etch profiles for the validation set. If the error between experimental and theoretical etch profiles for the validation set is statistically higher than the error found at convergence using the training set, a different training set is used to tune the model as before.

Details Regarding Iterative Non-Linear Optimization Procedures

The model parameter optimization procedure just described in the context of FIG. 3 is generally an iterative non-linear optimization procedure—e.g., it optimizes an error metric which is, in general, a non-linear function of the input parameters—and, as such, various techniques known in the art for non-linear optimization may be employed. See, for example: Biggs, M. C., "Constrained Minimization Using Recursive Quadratic Programming," Towards Global Optimization (L. C. W. Dixon and G. P. Szergo, eds.), North-Holland, pp 341-349, (1975); Conn, N. R., N. I. M. Gould, and Ph. L. Toint, "Trust-Region Methods," MPS/SIAM Series on Optimization, SIAM and MPS (2000); Moré, J. J. and D. C. Sorensen, "Computing a Trust Region Step," SIAM Journal on Scientific and Statistical Computing, Vol. 3, pp 553-572, (1983); Byrd, R. H., R. B. Schnabel, and G. A. Shultz, "Approximate Solution of the Trust Region Problem by Minimization over Two-Dimensional Subspaces," Mathematical Programming, Vol. 40, pp 247-263 (1988); Dennis, J. E., Jr., "Nonlinear least-squares," State of the Art in Numerical Analysis ed. D. Jacobs, Academic Press, pp 269-312 (1977); Moré, J. J., "The Levenberg-Marquardt Algorithm: Implementation and Theory," Numerical Analysis, ed. G. A. Watson, Lecture Notes in Mathematics 630, Springer Verlag, pp 105-116 (1977); Powell, M. J. D., "A Fast Algorithm for Nonlinearly Constrained Optimization Calculations," Numerical Analysis, G. A. Watson ed., Lecture Notes in Mathematics, Springer Verlag, Vol. 630 (1978); each of which is hereby incorporated by reference in its entirety for all purposes. In some embodiments, these techniques optimize an objective function (here the error function/metric) subject to certain constraints which may be placed on the input parameters and/or the error metric. In certain such embodiments, the constraint functions themselves may be non-linear.

For example, in embodiments where the computed etch profile is represented with a set of stacked trapezoids which are output by the EPM, the error metric may be defined as the difference between the area represented by the boundaries of these stacked trapezoids and the area of the measured experimental etch profile. In this case, the error metric is a non-linear function of the response variables output by the EPM, and thus a constrained optimization technique is selected from those just described (and/or from the incorporated references) which allows for the specification of non-linear constraints. Note that in the context of the flowchart presented in FIG. 3, these various procedures correspond to how the one or more model parameters are modified in operation 360, and also how one or more potential local minima in error are detected and treated in operation 350.

In some embodiments, an iterative non-linear optimization procedure which is used to determine improved/tuned model parameters as shown in FIG. 3 may be divided into multiple phases, and in certain such embodiments, the different optimization phases may correspond to different layers of material on the surface of the semiconductor substrate being etched. This approach may also reduce the computational burden by reducing the number of input parameters being varied and simplifies the error metric being calculated. For instance, if the substrate to be etched includes a multi-layer stack of different sequentially deposited materials, because the different layers, in general, have different material compositions, in general, different chemistries characterize the local etch process occurring in each layer—e.g., a different etch reaction (or reactions), different side reactions, different reactions between by-products, or even if the same (or similar) chemical reactions are occurring, they may generally be occurring at different rates, in different stoichiometric ratios, etc. Thus, in order to setup an etch profile model (EPM) corresponding to the etching of the whole multi-layer stack, input parameters fed into the model generally include different sets of parameters corresponding to the different stacked layers. As described above, these sets may include parameters indicating which chemical reactions are to be included in the modeling of the etch processes, as well as parameters characterizing the reactions themselves—reaction probabilities, sticking coefficients, and the like.

However, it is recognized that an optimization protocol does not necessarily need to optimize every parameter simultaneously, e.g. some may remain fixed in operation 360 of FIG. 3 while others are allowed to "float" and be modified in one or more particular cycles/rounds of optimization as schematically illustrated in the figure. Therefore, based on the observation that the chemical processes occurring in each layer are to a certain extent local to that layer, in some embodiments, optimization may be accelerated by tuning the model parameters associated with one layer, individually, while holding the parameters associated with the other layers fixed, and thereafter selecting another layer, allowing its parameters to "float," while holding those for the others fixed, and so forth, until all layers have been individually tuned. The layer-by-layer tuning process may then repeated multiple times, each time cycling through all the layers, until a certain degree of optimization is attained, and at this point, a full optimization over all layers may be performed—i.e., allowing the model parameters for all the layers to be varied/"floated"—based on the recognition that the full optimization will converge more efficiently (and possibly to a better local minimum in the error metric) with the parameters associated with each layer having been individually optimized. Going one step further, the entire layer-by-layer procedure may be repeated to improve results further—i.e., performing layer-specific optimization by cycling through the layers one or more times, and then performing a global optimization, which allows the model parameters of all layers to float. Note that, in the context of FIG. 3, the selection of certain model parameters and allowing them to "float" (and thus be individually optimized for a specific layer) while others are held fixed, would be done as part of the parameter modification operation 360 of FIG. 3 (in these and similar classes of embodiments).

As a specific example illustrating the foregoing individual layer-by-layer optimization procedure, consider the case of modeling the etching of a layer underneath an etch mask, where both the etch mask layer and the layer beneath it are etched to some extent. This thus constitutes a 2-layer etch model where the parameters for each of the two layers may be individually optimized prior to full simultaneous optimization of the model parameters corresponding to both layers.

Therefore, one begins by specifying values for all the model parameters, running the model to generate computed etch profiles over all the sets of values of the input parameters—representing different experimental etch conditions—and calculating an error metric indicative of the difference between the experimental and computed etch profiles over all the profiles corresponding to the multiple sets of values for the independent input parameters. One may then proceed by selecting the layer beneath the etch mask—say a layer of dielectric—for individual layer-specific optimization, modifying one or more model parameters associated with this (dielectric) layer for optimization, re-running the model over all sets of values of the independent input parameters, calculating a new error metric, again modifying one or more model parameters associated with the dielectric layer, re-running the model, recalculating the error, and so forth, until a local minimum in error is obtained with respect to the dielectric layer.

The model parameters for the dielectric layer are then held fixed at these values, the model parameters of the etch mask layer are selected for individual optimization, one or more of their values (of the model parameters of the etch mask layer) modified, the model re-run, the error recalculated, and so forth until a local minimum in error is achieved with respect to the etch mask layer. At this point, a full optimization over the model parameters of both layers may be performed, or in some embodiments, before doing that, one or more additional cycles of individual dielectric layer and mask layer optimization may be performed so that the full optimization is more effective (e.g., converges faster, or converges to a better resulting local minimum in the total error metric).

It should also be understood, that in some cases, the foregoing layer-by-layer optimization procedure doesn't necessarily have to be restricted to the tuning of only a single individual layer at one time. For instance, if one were modeling the etching of a 6-layer stack, one variation of the foregoing layer-by-layer optimization procedure would be to select pairs of layers for simultaneous tuning—i.e., floating the model parameters corresponding to pairs of adjacent layers simultaneously—and do this sequentially for the 3 pairs, possibly repeat the 3-step cycle multiple times, before then performing the full simultaneous optimization over model parameters for all the layers; as before, optionally, repeating the entire layer-by-layer procedure (or, in this case, pairwise layer-by-layer procedure) until a local minimum in error over the entire stack is identified.

It is also possible that the numerical optimization procedure (whether performed on a layer-by-layer basis before full optimization, or performed directly as a full optimization over all layers) may result in multiple local minima in the etch profile metric depending on the starting point of the optimization (i.e., depending on the initial values chosen for the model parameters), as well as other factors, and thus there may be many local minimum which the optimization procedure could potentially identify as representing the improved (and/or optimal model). In the case of many local minima in error, many potential sets of model parameters may be eliminated from consideration by defining physically realistic upper and lower boundaries for these model parameters. In some embodiments, the foregoing numerical optimizations may be performed for a plurality of choices for starting points (initial values for the model parameters) in order to potentially identify a plurality of local minima, and thus a plurality of candidate sets of model parameters, from which the most preferred may be chosen (possibly, in some embodiments, because it has the lowest computed error metric of all the candidates which satisfy the foregoing mentioned physically realistic upper and lower bounds).

Dimensionality Reduction and Principle Component Analysis

In some embodiments, an etch profile model outputs values at a large number grid/mesh points (cells) at each time step during the calculated etch profile evolution. These values corresponding to each cell or grid point map out the shape of the calculated etch profile. Such an example of a grid/mesh of points representing a computed etch profile are illustrated in FIG. 1, where each grid/mesh point has a value indicating whether or not that region of space is occupied by the feature at that time during the etch process. In some embodiments, the vertical dimension of the mesh representing an etch profile is at least about 5, or at least about 10, or at least about 20. Depending on the embodiment, a minimum value for the vertical distance between vertically adjacent mesh points may be chosen to be 1 Å and can be as large as a few angstroms, such as 5 Å, or 10 Å, or even 20 Å.

In practice, one would like to choose the distance between adjacent mesh/grid points to be small enough to provide a reasonably accurately representation of the shape of the feature as it evolves in time (which likely depends on the intricacy of the profile), but not much (or any) smaller than necessary to achieve this reasonable representation (because more grid points entail more compute time). The horizontal separation (in the plane of the wafer) between adjacent mesh/grid points would be chosen based on the same considerations, but in general horizontal and vertical separation would be chosen to be the same (i.e., a uniform grid) or roughly comparable. This does not mean the vertical and horizontal grid dimensions are necessarily the same, however, because the width the of the feature being modeled is not necessarily the same as the height of the feature which is being modeled. Thus, the horizontal dimension (number of horizontal points spanning a given direction, x-dimension in 2D, x- and y-dimensions in 3D), may depend on whether just a sidewall of a feature is being modeled, whether the entire feature is being modeled (it's span from one profile edge to another), whether multiple adjacent features are being modeled, etc.

As stated, the mesh of values which are output by the etch profile model provide an estimation of where, in physical space, the edge of the feature profile is located at different vertical elevations. From this information (from these values at the mesh points) one can compute a feature width at different elevations, or in another view, a horizontal coordinate of the edge (relative to some baseline) for each elevation. This is illustrated in FIG. 2. This set of coordinates may then be viewed as a point in multi-dimensional space representing the particular feature profile. This vector space may be an orthogonal space, or it may be a non-orthogonal space, however a linear transformation may be made of this representation to an orthogonal space. If so, then the transformed point's coordinates are distances in relation to a set of orthogonal axes in that space. In any event, when "profile coordinates" are referred to in this document, this refers generally to any appropriate (approximate) mathematical representation of the profile shape.

In any event, because the etch profile model may output a large number of "profile coordinates" (hereinafter inclusive of a grid/mesh of points as just described) and the goal is to have these accurately match the measured experimental etch profiles, reducing the error in the etch profile model—iteratively reducing the error combined over the different experimental process conditions as described with respect to FIG. 3 above—may be a computationally demanding task. For example, if a set of m measured experimental etch profiles are to be matched point-by-point to calculated etch profiles consisting of n profile coordinates, then this amounts to optimizing a model to fit a dataset m×n data points.

Figure 5:
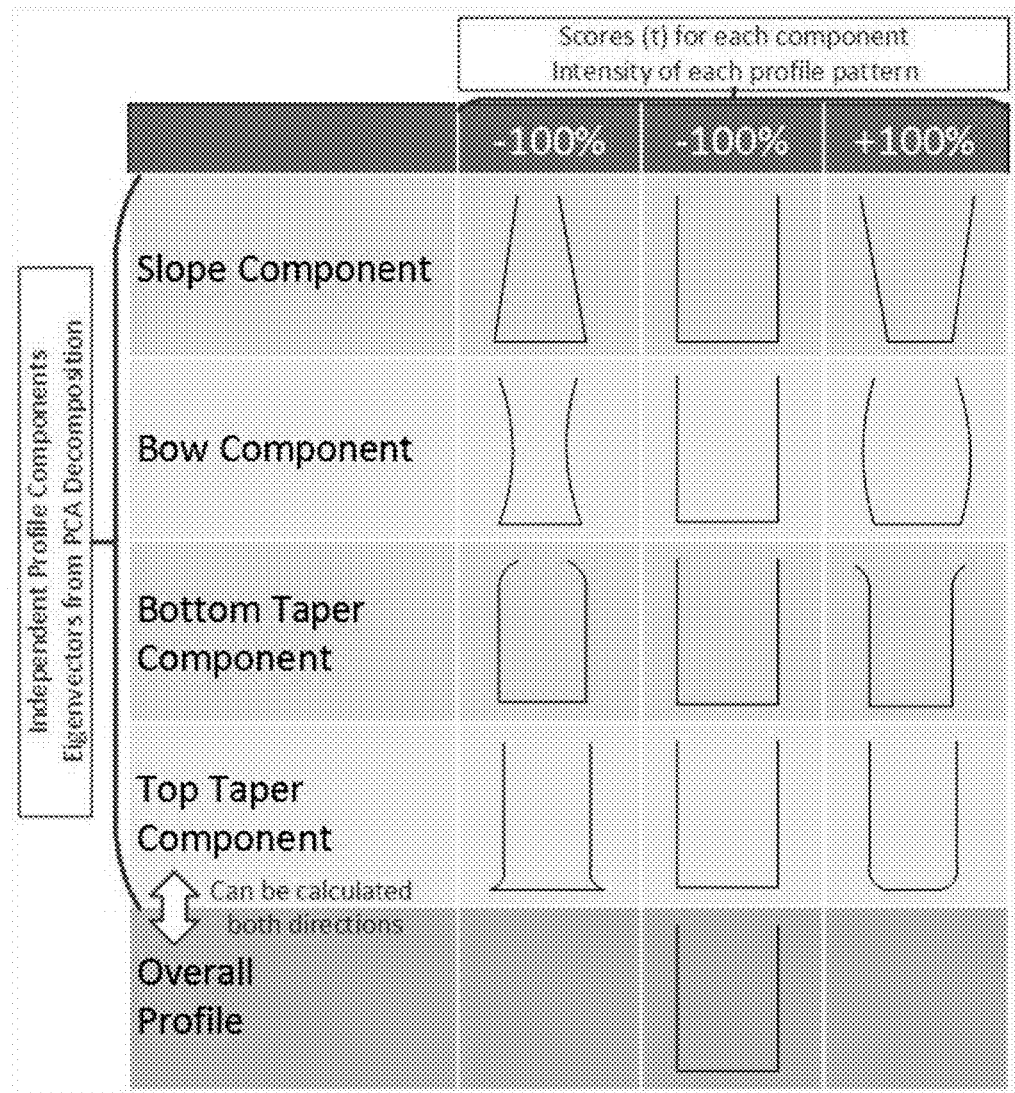
FIG. 5 depicts an example set of canonical etch profiles that may be identified using models optimized in accordance with this disclosure.

It turns out, however, that there are latent statistical correlations in the etch profiles (whether measured or calculated) and that one may take advantage of these correlations to recast the optimization problem in a form which is far more numerically tractable. For instance, while a fine grid of profile coordinates may consist of many data points, from a statistical viewpoint, the values of certain combinations of these coordinates are correlated with one another. To give a trivial but illustrative example, vertically adjacent coordinates will tend to be correlated with one another—simply because the width of an etched feature is not going to change too drastically over the short length scale associated with adjacent grid points as one moves up or down the profile. More complicated examples of correlations between profile coordinates relate to the types of profile shapes which may generally be achieved by varying certain combinations of process parameters. Several examples are shown in FIG. 5. For instance, certain process parameters, alone or in combination with one another, may be adjusted to cause an etched profile to be bowed either inward or outward, as shown in FIG. 5, and the profile coordinates (or grid points) which map out this bowing of the profile are thus statistically correlated with one another. Likewise, as also shown in FIG. 5, etch profiles obtained through adjustment of various process parameters, individually or in combination, may exhibit a downward or upward taper, and thus profile coordinates may be correlated to the extent that varying one or more process parameters tends to cause this tapering effect. Two other examples of underlying profile correlation structures are top taper and bottom taper, as also illustrated in FIG. 5. Again, these underlying profile structures are manifestations of the fact that variations in process parameters tend to cause changes in the overall shape of the profile rather than having a local effect at certain spots on the profile without affecting other spots. This is, of course, a consequence of the underlying physics and chemistry associate with the etch process.

As mentioned, because of these underlying statistical correlations, the optimization problem presented above (described with respect to the flowchart in FIG. 3) can be recast in a form which is more amenable to iterative optimization techniques. One way of doing this is to identify several types of canonical profiles shapes, and express the measured and/or computed etch profile in terms of these canonical shapes—such as by writing the total profile (at each profile coordinate) as a weighted average of the set of canonical profile shapes (at each profile coordinate). I.e., a set of vectors represents the canonical profile shapes and the total profile may be approximately expressed as a linear combination of these vectors. In this manner, one can take advantage of the underlying statistical correlations and model changes in the coefficients/weights of the linear combination representing the profile, rather than model the changes in all the individual profile coordinates. For example, if one were to choose bow and taper (see FIG. 5) as the canonical shapes, then the problem of modeling say m=100 profile coordinates is reduced to modeling changes in the 2 coefficients for bow and taper in the linear combination—i.e., constituting a dimensionality reduction from 100 to 2. Which canonical shapes are useful may depend on the process/layer type. The depicted methods provide a numerical way of extracting those shapes from either experimental data or from performing simulations with EPMs.

For this strategy to be effective the canonical shapes must provide a good, albeit not exact, representation of the different profile shapes involved in the analysis. The more independent canonical shapes included in the representation, the more accurate the representation will be (in the vector space of the canonical shapes). Thus, the question becomes what canonical shapes to use, and how many to include, recognizing that including more canonical shapes makes the analysis more accurate, but it also makes it more computationally expensive, and in the context of iterative optimization, it may affect the ability of the optimization to converge, or to converge as desirable a local minimum.

One way of doing this is to have process engineers identify a few types of canonical profiles shapes which they observe, based on their past experience, to frequently occur in their etch experiments. The advantage of this approach is that it is simple. A potential disadvantage is that it is ad hoc (being simply based on the experience and intuition of the process engineer) and that it does not provide any way of determining when a sufficient number of profile shapes have been included in the analysis. In practice, any canonical profile shape that a process engineer identifies will get included, but this may, of course, be insufficient to provide an accurate representation. More importantly, this type of methodology will not identify new correlations in the profile data which have not previously been identified, either because in previous work the shape was not as pronounced, or because it is a result of a new etch process with different underlying physical and chemical processes taking place.

Another approach is to base the dimensionality reduction procedure on a statistical methodology which can automatically identify the important canonical profile shapes as well as to provide an estimate of how many shapes need to be included in order to provide a sufficiently accurate representation. One data analysis technique for achieving this is principle component analysis (PCA), which makes use of the singular value decomposition (SVD), a matrix decomposition technique from numerical linear algebra. A description of the PCA technique and various applications may be found (for example) in: Jackson, J. E., "A User's Guide to Principal Components," John Wiley and Sons, p. 592. [2] (1991); Jolliffe, I. T., "Principal Component Analysis," 2nd edition, Springer (2002); Krzanowski, W. J., "Principles of Multivariate Analysis: A User's Perspective," New York: Oxford University Press (1988); each of which is hereby incorporated by reference in its entirety for all purposes.

As described in the foregoing references, PCA takes as its input a set of vectors—in this case each vector being a series of n etch profile coordinates representing a single profile—and returns a new set of n orthogonal vectors known as the principal components (PC) which may be sorted so that PCs 1–i (where i≤n) constitute the "best" ith dimensional subspace for representing the input profile vectors; "best" means statistically optimal in the least squares sense—i.e. that the ith-dimensional subspace of PCs determined from the PCA minimizes the combined RMS error between each input vector and its linear representation in the subspace of the selected PCs. Of course, the more PCs which are included, the larger the dimension of the subspace and the better the representation of the input profile data; however, because a subspace constructed via PCA is optimal, the expectation is that not many PCs are required—and the amount of statistical variation in the underlying data which is captured by adding an additional PC may be assessed through the singular values of the underlying SVD. Thus, by using PCA to identify the canonical profile shapes which underlie a dataset of etch profiles, one can construct a reduced-dimensional linear model for representing the etch profiles, and do so in a fashion which is automatic (does not rely on the expertise of the process engineer) and has the ability to identify new correlations in the profile data, and in a manner which provides a statistical estimate of how many shapes/dimensions are required to provide a good representation.

The result of the foregoing methodology is that a significant dimensionality reduction may be achieved without significantly compromising statistical error and that the number of data points required for fitting in the numerical optimization procedure described above may be substantially reduced. It is also noted that there are different viable strategies for implementing the dimensionality reducing PCA procedure within the optimization procedure presented in FIG. 3. For instance, in the context of the manner in which the error metric is calculated in operation 340 of FIG. 3, one way to employ a dimensionality reduction procedure is to project the computed and corresponding experimental etch profiles, individually, onto a reduced-dimensional subspace (which may be constructed via PCA), and then to calculate the difference between the profiles as projected onto the subspace. Another way is to take the differences between the computed and corresponding experimental etch profiles, project the differences onto a reduced dimensional subspace representative of the potential differences between experimental and calculated etch profiles, and view the total error metric as the combined lengths of these vectors in the difference-sub space.

It is additionally noted that PCA may also be used to dimensionally reduce the number of independent variables in the space of independent input parameters, providing a similar benefit to that just described. In some embodiments, the dimensionality reduction procedure may be applied to both the profile coordinate space and the input parameter space, simultaneously, such as, for example, by performing a PCA on the concatenated vectors of input parameters and corresponding measured etch profiles.

Applications of the Optimized Computerized Etch Model

The optimized computerized etch models disclosed herein may be useful in semiconductor processing workflows wherever a detailed assessment and characterization of an etch process is desirable. For instance, if a new etch process is being developed, the model may be used to determine etch profile characteristics for many combinations of process parameters without having to go into the lab and perform each experiment individually. In this way, the optimized etch profile models may enable quicker process development cycles, and in some embodiments may significantly reduce the amount of work required to fine tune a target profile.

Lithographic operations and mask development may also benefit greatly from accurate etch profile modeling because estimating edge placement error is typically quite important in lithographic work, and an accurate calculation of profile shape provides that information.

The optimized models disclosed herein may also be useful for solving the reciprocal problem: where one desires a specific target etch profile and wants to discover one or more specific combinations of process parameters (or EPM input parameters) for achieving it. Again, this could be done by experimental trial and error, but an accurate modeling of the etch profile that results from a given set of process parameters (or EPM input parameters) and conditions can replace the need for experimentation, or at least do so in the initial phases of exploring the process/input parameter space, until good candidates may be identified for full experimental study. In some embodiments, it may be possible to, in effect, numerically invert the model—i.e., iteratively locate a set of parameters which generate a given etch profile—in a fully automated fashion. Once again, dimensionality reduction of the etch profile coordinate space (via PCA), and projection of the desired etch profile onto this space, may make this numerical inversion more feasible.

In certain embodiments, an optimized EPM may be integrated with an etcher apparatus or into the infrastructure of a semiconductor fabrication facility which deploys one or more etcher apparatuses. The optimized EPM may be used to determine appropriate adjustments to process parameters to provide a desired etch profile or to understand the effect of a change in process parameters on the etch profile. Thus, for instance, a system for processing semiconductor substrates within a fabrication facility may include an etcher apparatus for etching semiconductor substrates whose operation is adjusted by a set of independent input parameters which are controlled by a controller which implements an optimized EPM. As describe below, a suitable controller for controlling the operation of the etcher apparatus typically includes a processor and a memory, the memory storing the optimized EPM, and the processor using the stored EPM to compute etched feature profiles for a given set of values of a set of input process parameters. After computing a profile, in some embodiments, the controller may (in response to the shape of the computed profile) adjust the operation of the etcher apparatus by varying one or more values of the set of independent input parameters.

Generally, an etcher apparatus which may be used with the disclosed optimized EPMs may be any sort of semiconductor processing apparatus suitable for etching semiconductor substrates by removing material from their surface. In some embodiments, the etcher apparatus my constitute an inductively-coupled plasma (ICP) reactor; in some embodiments, it may constitute a capacitively-coupled plasma (CCP) reactor. Thus, an etcher apparatus for use with these disclosed optimized EPMs may have a processing chamber, a substrate holder for holding a substrate within the processing chamber, and a plasma generator for generating a plasma within the processing chamber. The apparatus may further include one or more valve-controlled process gas inlets for flowing one or more process gases into the processing chamber, one or more gas outlets fluidically connected to one or more vacuum pumps for evacuating gases from the processing chamber, etc. Further details concerning etcher apparatuses (also generally referred to as etch reactors, or plasma etch reactors, etc.) are provided below.

Optimization of the Etch Profile Models by Reflectance Spectra Matching Techniques The etch profile (EP) model (EPM) optimization techniques disclosed herein may also be performed in the reflectance spectral space, or a reduced dimensional subspace (RDS) derived from the space of spectral reflectances. In other words, the EPM optimization is done by matching calculated reflectance spectra (generated with the EPM) to experimentally measured reflectance spectra, each spectra representing the intensity of electromagnetic radiation reflected from an etched feature on the substrate surface at a series of wavelengths. The set of reflectance spectra used for the optimization (both the spectra generated via EPM and measured experimentally) may also correspond to a sequence of etch time steps (i.e., representing different time snapshots of an etch process or processes). As discussed in detail above, EPMs generally compute a theoretical etch profile as it evolves in time during an etch process, and so by including reflectance spectra from different etch time step in the optimization, the optimized model is statistically valid over the sequence of etch times used in the optimization.

The spectral matching (SM) optimization procedure follows the general EPM optimization framework described above, e.g., in reference to FIG. 3, the difference being that the SM optimization operates in terms of spectral reflectances instead of etch profile coordinates. To do this—because the typical output of an EPM is a computed etch profile represented by a series of etch profile coordinates—one generates computed reflectance spectra by simulating the reflection of electromagnetic radiation (EM) off of said computed etch profile. What is known in the art as "rigorous coupled wave analysis" (RCWA) constitutes one computational process which may be used for this purpose, but any suitable procedure for simulating the interaction of EM radiation with the substrate feature under consideration may be employed.

In any event, with the ability to generate reflectance spectra from an EPM, a general procedure may be implemented for optimizing said EPM in terms of spectral reflectances. This is now described with respect to FIG. 6 which presents a flowchart illustrating a set of operations 601 for tuning and/or optimizing an etch profile model.

As above, and in some embodiments, such a tuned and/or optimized model reduces—and in some cases substantially minimizes—a metric which is related to (indicative of, quantifies, etc.) the combined differences between the etch profiles which are measured as a result of performing the etch experiments, and the corresponding computed etch profiles as generated from the model. In other words, an improved model may reduce the combined error over the different experimental process conditions (as designated by the different sets of specified values of the selected process parameters—which are used to compute independent input parameters to the EPM).

Figure 6:
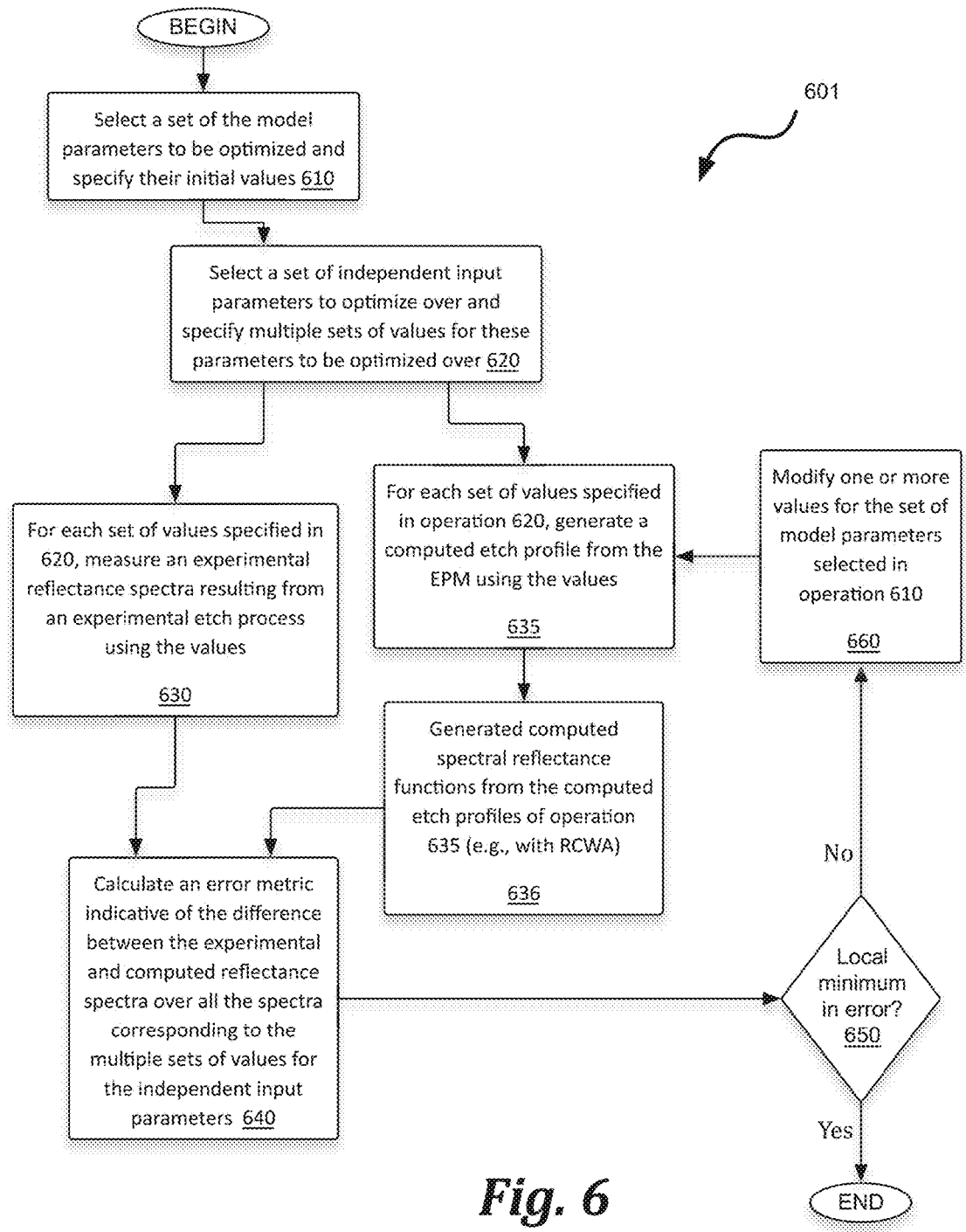
FIG. 6 is a process flow chart representing procedures for optimizing etch profile models with respect to a reflectance spectral space.

As shown in FIG. 6, the reflectance spectra-based optimization procedure 601 begins at operation 610 with the selection of a set of model parameters to be optimized and the specification of their initial values—again, these model parameters may be chosen to be parameters which characterize the underlying chemical and physical processes (reaction probabilities, sticking coefficients, etc.), some or all of these will be adjusted based on the experimental data to improve the model. The initial values may be those found in the literature, they may be calculated based on other simulations, determined from experiment, or known from previous optimization procedures, etc.

The model parameters chosen and initialized in operation 610 are then optimized over a set of independent input parameters, which are selected and given multiple sets of values in operation 620. Such independent input parameters may include, for example, parameters which characterize the plasma in the reaction chamber: temperature, etchant flux, plasma density, etc. For each combination of values of independent input parameters, in operation 630 an etch experiment is performed in order to measure an experimental etch reflectance spectra. (In some embodiments, multiple etch experiments are performed for the same combination of values for the input parameters and the resulting reflectance spectra measurements are averaged together (possibly after discarding outliers, noisy spectra, etc.), for example.) This set of benchmarks is then used for tuning and optimizing the model as follows: In operations 635 and 636 a set of computed reflectance spectra are generated—which correspond to the measured spectra from operation 630 and thus are generated for each combination of values of the input parameters—by running the EP model to yield an etch profile, and then converting the computed etch profiles to spectral reflectances as described above (e.g., by using RCWA). At this point, there are corresponding experimental and computed reflectance spectra generated from each set of chosen values for the independent input parameters, and thus suitable for comparison. The comparison is done in operation 640, where an error metric is calculated which is indicative of (related to, quantifies, etc.) the difference between the experimental and computed reflectance spectra over all the different sets of values for the input parameters.

Analogously to what was described above with respect to FIG. 3, this set of computed reflectance spectra (from which the error metric is calculated) corresponds to a set of previously chosen model parameters as specified in operation 610. A goal of the optimization procedure is to determine more effective choices for these model parameters. Thus, in operation 650 it is determined whether the currently specified model parameters are such that the error metric calculated in operation 640 is locally minimized (in terms of the space of model parameters), and if not, one or more values of the set of model parameters are modified in operation 660, and then used to generate a new set of reflectance spectra—repeating operations 635 and 636 as schematically indicated in FIG. 6's flowchart—and thereafter a new error metric is calculated in a repeating of operation 640. The process then proceeds again to operation 650 where it is determined whether this new combination of model parameters represents a local minimum over all the sets of input parameters as assessed by the error metric. If so, the optimization procedure concludes, as indicated in the figure. If not, the model parameters are again modified in operation 660 and the cycle repeats.

If it is desired that the EPM be optimized (in the foregoing manner) for etch processes of different time durations, or be optimized for computing reflectance spectra at sequences of times over the course of an etch process, a consideration is the extent to which the experimental reflectance spectra used to optimize the EPM may be determined accurately from optical measurements over the course of an etch process. A related issues is the rate at which these measurements may be performed over the course of the etch process.

Broadly, measurements of spectral reflectance may be performed in situ or ex situ. Ex situ measurements are generally more accurate due to employment of an external dedicated metrology tool (external to the etch chamber), but such measurements require that the wafer be removed from the etch chamber and thus that the etch process be stopped in order to utilize the tool. Since stopping and re-starting an etch process would lead to all sorts of systematic errors relative to an etch process of continuous duration, accumulating reflectance spectra for a sequence of different etch times ex situ generally involves etching a sequence of different wafers each for a different desired duration and then measuring reflectance form each individually. On the other hand, in situ spectral reflectance measurements may be made continuously (or substantially continuously, or at least quite rapidly) without interrupting the ongoing etch process, and thus a single wafer can be used to generate reflectance spectra corresponding to a sequence of etch times (which also eliminates (or at least reduces) the possibility of wafer-to-wafer variation being interpreted as representing the etch time-dependence of the reflectance spectra). However, wafer-to-wafer variation aside, for a variety of reasons, in situ spectral reflectance measurements tend to be less accurate than when a dedicated external metrology tool is used.

Disclosed here, however, is a way to attain (at least to a certain extent) the advantages of both ex situ and in situ spectral reflectance measurements without their respective drawbacks. In particular, the strategy is to use experimental reflectance spectra for optimizing the EPM which have been generated from rapid in situ spectral reflectance (optical) measurements taken during ongoing etch processes (at the sequence of etch times desired to optimize the EPM) that are calibrated using ex situ measurements taken with a dedicated metrology tool.

This may be done as follows. One or more wafers are etched for a duration covering the desired sequence of etch times, and throughout the ongoing etch processes spectral reflectance optical measurements are taken in situ. The measurement rate may be quite rapid, for example with a frequency of 1 Hz, 2 Hz, 5 Hz, 10 Hz, 15 Hz, 20 Hz, 50 Hz, or even 100 Hz. In some embodiments, optical measurements taken at consecutive etch times over at least a portion of the sequence of etch times are separated by 0.01-1 second (i.e., with a frequency of 100 Hz to 1 Hz), or are separated by 0.05-0.5 second (i.e., with a frequency of 20 Hz to 2 Hz). Separately, a set of wafers are etched for different specified etch durations, and after each etch process is concluded, and the wafers removed from the processing chambers in which they were etched, reflectance spectra are optically measured ex situ with a dedicated external metrology tool. The in situ measurements at the different etch times are then calibrated by comparing them to the ex situ measurements of corresponding duration, and adjusting the in situ reflectance spectra intensities accordingly. These reflectance spectra, generated from in situ optical measurements calibrated with ex situ optical measurements, may then be used in the EPM optimization described with respect to FIG. 3.

The optimization procedure may also be performed with respect to a reduced-dimensional subspace (RDS)—similar to what was done with respect to the etch profile space, but in this case, a dimensionality reduction of the spectral space—which involves using the RDS to calculate the error metric which is minimized (usually locally, or approximately so) in the optimization. One way of constructing the RDS is by way of PCA whereby, instead of doing the PCA in the space of etch profile coordinates as was described above, the PCA may be done on the full space of spectral reflectances. In so doing, a significant dimensionality reduction of the spectral space may be achieved without significantly compromising the statistical error in the numerical optimization. Here, the PCA may identify important canonical spectral shapes, and it also (as described above) provides an estimate of how many shapes should be included to achieve some level of desired statistical accuracy. In this manner, as when done in the etch profile coordinate space, the number of data points required for fitting in the numerical optimization procedure may be significantly reduced, and convergence of the numerical optimization achieved more rapidly.

Likewise, and similarly to the case of optimization in the etch profile coordinate space, it is also noted that there are different viable strategies for implementing the use of a RDS, e.g., within the optimization procedure presented in FIG. 6, whether the RDS is constructed via PCA, or PLS (as described below), or otherwise. Thus, for instance, in the context of the manner in which the error metric is calculated in operation 640 of FIG. 6, one way to employ a dimensionality reduction procedure is to project the computed and corresponding experimental spectral reflectances, individually, onto the RDS, and then to calculate the difference between the reflectance spectra as projected onto the subspace. Another way is to take the differences between the computed and corresponding experimental reflectance spectra, and then project the differences onto a reduced dimensional subspace representative of the potential differences between experimental and calculated reflectance spectra; the total error metric is then viewed as the combined lengths of these vectors in the difference-subspace (of reflectance spectra).

Rather than perform a PCA, another way to construct the RDS is simply to select a particular set of spectral wavelengths and to consider these (selected wavelengths) as the basis set for the RDS. Doing this, projecting two reflectance spectra onto the RDS and calculating their difference (in the RDS) amounts to calculating the difference in intensity of the reflectance spectra at those particular wavelengths and, for example, summing the differences, which would then make the error metric a number proportional to the root mean square (RMS) error (over those wavelengths). Generalizing this, the error metric may be given as a weighted sum of quantities monotonically related to the magnitude of the differences between corresponding experimental and calculated reflectance spectra at the particular selected wavelengths.

Moreover, if the experimental and computed reflectance spectra to be compared in the optimization procedure correspond to a sequence of different etch times, then an additional criteria defining the RDS may be the selection of these particular etch times. Thus, in such embodiments, the RDS is determined based on a selection of particular spectral wavelengths and the identification of particular etch times at which the wavelengths are considered. Moreover, in certain such embodiments, the different wavelengths and etch times may be weighted differently in the calculation of the error metric. Thus, for example, if the spectral data at certain etch times is more probative than the data at other etch times, then (some of) the former may be weighted more heavily (i.e., particular wavelengths at particular etch times may be set to be larger than (some of) the weights corresponding to the same wavelengths at other etch times). Additionally (or alternatively), different wavelengths of the reflectance spectra may be weighted differently in the analysis, even at the same etch times.

Figure 7A:
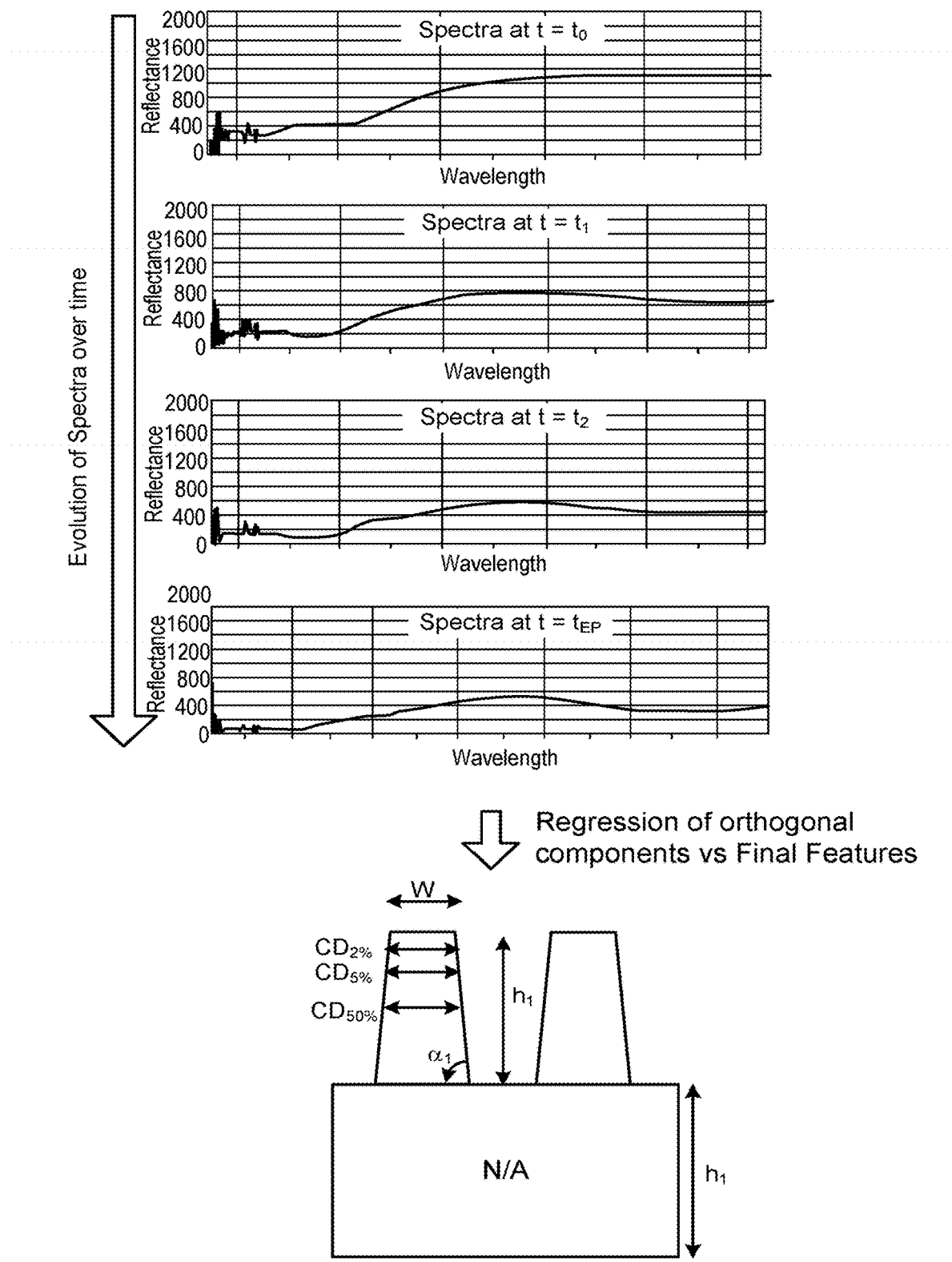
FIG. 7A is an illustration of the reflectance spectral history of an etch profile as it evolves during an etch process.

Another alternative for constructing the RDS is to perform a partial least squares (PLS) analysis. The PLS analysis takes advantage of the principle that the (reflectance) spectral history of an etch profile as it evolves during an etch process is predictive of the etch profile later in the etch process and/or at the conclusion of the etch process. An illustration is provided in FIG. 7A which shows 4 reflectance spectra corresponding to 4 sequential times during at etch process ($t_0$, $t_1$, $t_2$, and $t_{EP}$ ('EP' indicates feature's final etch profile)) as related to a feature (shown at the right in the figure) as the feature is etched downwards. From the figure, it is apparent that the reflectance spectra changes as the feature's profile changes over the course of the etch, and thus a statistical model may be generated via a PLS analysis which relates the geometric coordinates of a feature etch profile at the conclusion of an etch process with various reflectance values of particular wavelengths at particular times earlier in the etch process. The PLS analysis may identify which spectral wavelengths and at which times earlier in the etch processes are most predictive of the final etch profile, and the model may also assess the sensitivity of the final etch profile to these wavelengths and/or times. These spectral wavelengths at the particular times can then be designated as the basis set for the RDS with respect to which the EPM is optimized. Moreover, the PLS analysis's determination of the relative statistical significance of these designated wavelengths at particular times provides a basis for weighting them more heavily in the numerical optimization of the EPM, e.g., by defining the statistical weights in the error metric.

Stating it another way, a PLS analysis of geometric etch profile coordinates versus reflectance spectra from earlier in the etch process may be used to identify the sensitive spectral regions over the course of the etch process from which an effective RDS may be constructed, and the relative statistical weights given to these identified wavelengths at the identified prior etch process times may be used in the calculation of an error metric with respect to which the EPM parameter optimization is performed. It is noted that the use of such an RDS for the EPM optimization will presumably be efficient because it is targeted at statistically significant regions of the spectral space (as a function of etch time).

Figure 7B:
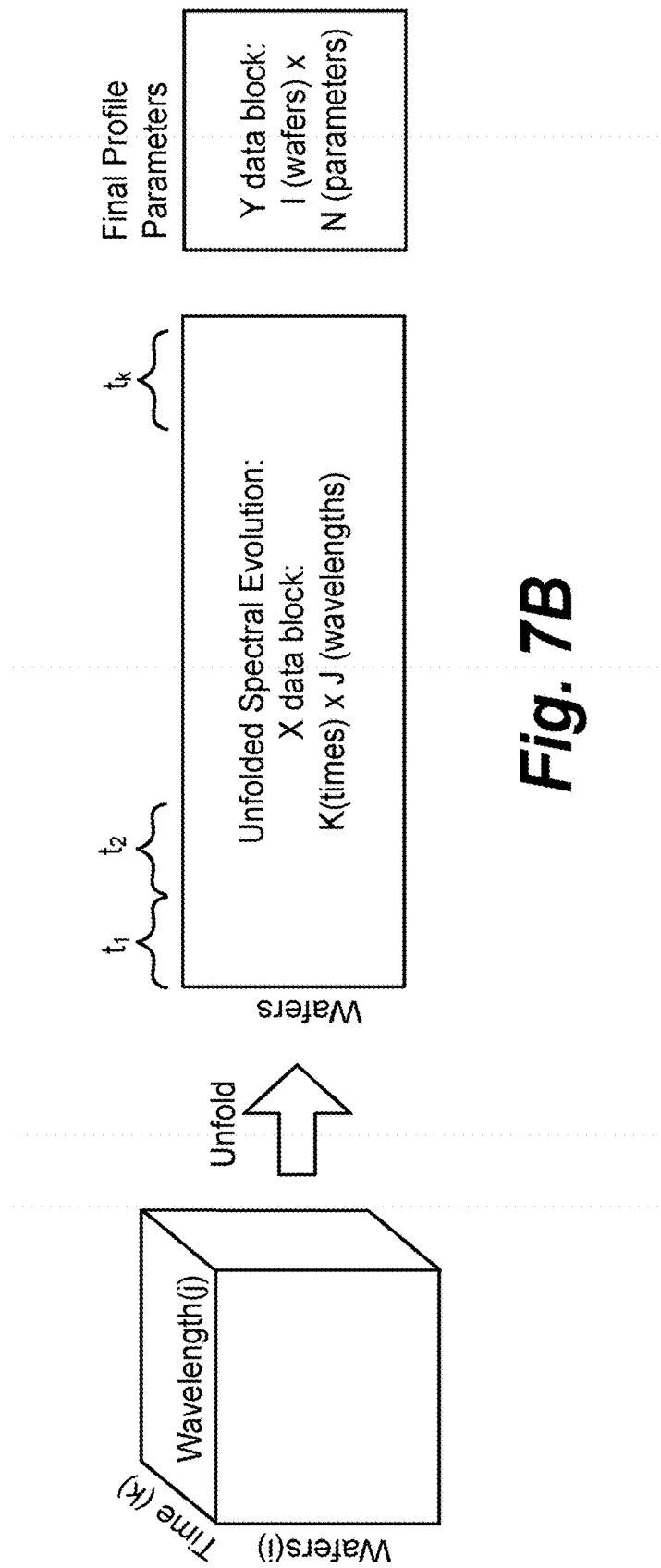
FIG. 7B schematically presents a set of spectral reflectance data collected over many wafers in the form of a 3-D data block (the 3 indices of the data block correspond to wafer number (i), spectral wavelength (j), and etch process time (k)); as well as the 3-D data block's unfolding into a 2-D data block which may serve as the independent data for the PLS spectral history analysis, the dependent data being the etch profile coordinates also indicated in the figure.

The foregoing PLS analysis and resulting PLS model (which provides a strategy for differentially weighting particular spectral wavelengths, etch times, etc.) will be more statistically robust if it is constructed from etch process data (sets of reflectance spectra and corresponding etch profile coordinates for different etch times) which are collected over many different wafers subject to a range of etch process conditions (which may roughly correspond to the range of process conditions over which the model parameters of the EPM are to be optimized (using the RDS)). FIG. 7B schematically presents such a set of reflectance spectral data collected over many wafers in the form of a 3-D data block where the 3 indices of the data block correspond to wafer number (i), spectral wavelength (j), and etch process time (k). This 3-D data block may be "unfolded," as indicated in the figure, into a 2-D "X" data block of size K times J, with K being the number of time points and J being the number of wavelengths. (The stride of the concatenated data vector is the number of wavelengths J.) These are the independent variables which go into the PLS analysis. The dependent variables for the PLS analysis are in the 2-D "Y" data block, as shown in the figure, which contains the final N geometric etch profile coordinates for each of the 1 number of wafers, as indicated in the figure. From this over-complete set of training data, the PLS analysis builds a regression model to predict the dependency of the final etch profile coordinates on the reflectance spectra data at intermediate times during the etch process.

Note that while such etch profile and spectral reflectance data (to be used as a training set for the PLS model) may be measured experimentally by performing etch processes on a series different wafers (and measuring reflectance), such experimentation may be costly and time consuming. However, if one already possesses an EPM of sufficient accuracy—such as one optimized by the procedure described above—a more efficient procedure may be to generate etch data sets using said EPM and to use them for constructing/training the PLS model. In principle, a combination of both experimental and computer generated etch profile and spectral reflectance data could also be used.

In any event, the use of computer generated reflectance spectra for building a PLS model suggests an iterative procedure whereby one uses a (potentially) un-optimized EPM to generate a training set of reflectance spectra for the PLS analysis, and the resulting PLS model may then be used to identify a RDS (with statistical weights) for returning to the initial EPM and optimizing it. The new optimized EPM may then, in turn, be used to generate new sets of etch data to construct a new (and better) PLS model, which identifies a new RDS for use in further optimizing the EPM, and so forth. The procedure may be continued in this manner (back and forth between EPM optimization and PLS optimization) for some predetermined number of iterations, or until significant improvement in the PLS and/or EP models is no longer found with subsequent iterations. A variation is to begin with an EPM optimized by any of the optimization techniques described above (e.g., not involving the PLS procedure) and go from there. Another variation is to use a few experimentally measured etch process data sets to construct the initial PLS model independent of the EPM, and then proceed to identify the RDS for optimizing the initial EPM. Other variations on these general themes, and combinations thereof, will be apparent to those of skill in the art in view of the foregoing discussion.

Figure 8:
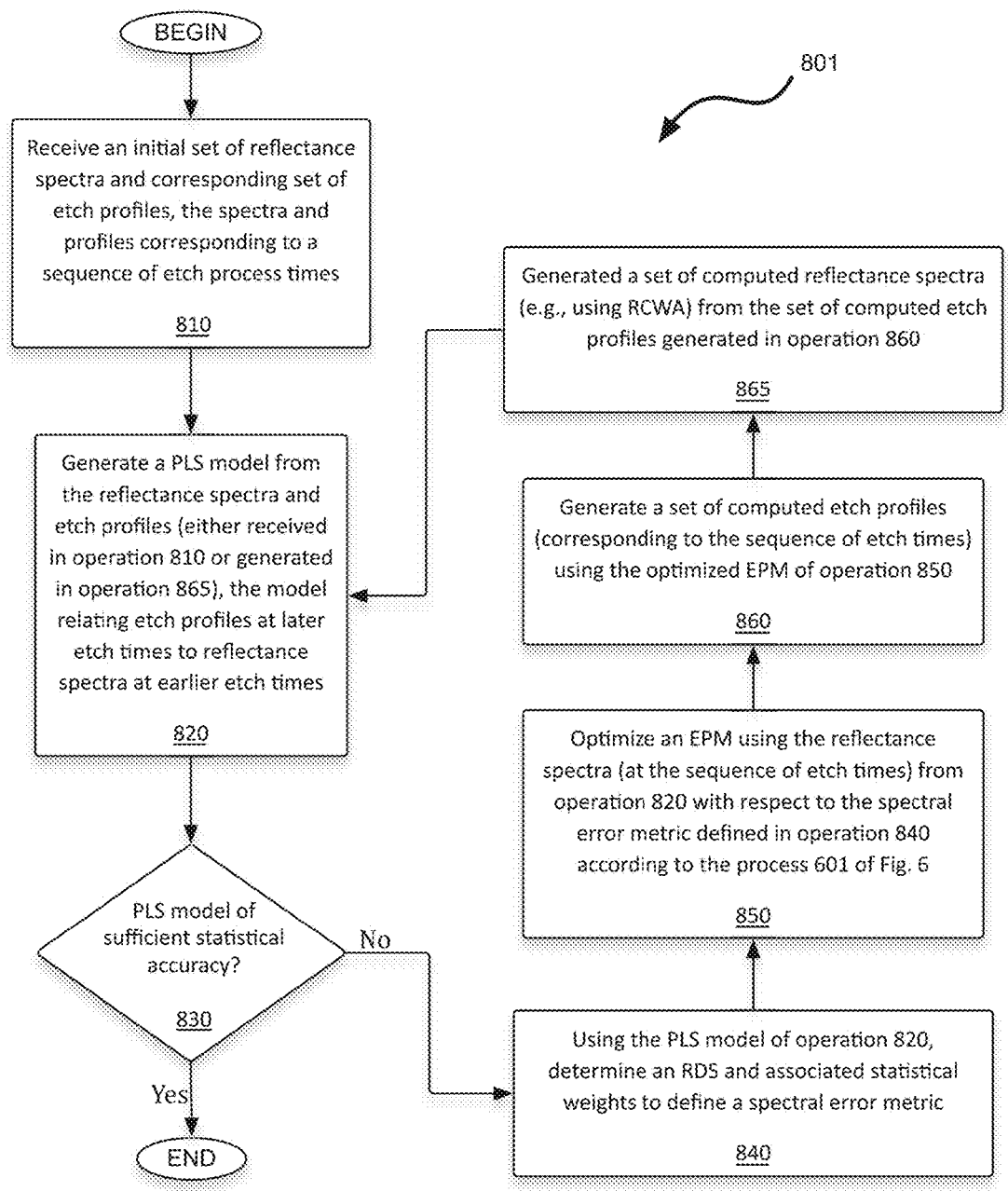
FIG. 8 is a process flow chart illustrating an iterative procedure for optimizing a PLS model relating etch spectral reflectance history to etch profiles over the course of an etch process while concurrently optimizing a EPM, which is used in the generation of computed reflectance spectra to be employed in the optimization of the PLS model.

This foregoing iterative approach is schematically illustrated in FIG. 8. As shown in FIG. 8, a process 801 of generating an optimized PLS model begins with an operation 810 of receiving an initial set of reflectance spectra and corresponding set of etch profiles, both of which correspond to a sequence of etch process time durations. The sequence of etch times could represent different times over the course of an etch process, or the sequence of etch times could represent etch processes of different total etch time durations (in other words, etch processes performed to completion but for different total etch times on different substrates). In any event, this initial training set of reflectance spectra (corresponding to the sequence of etch times) could have been measured experimentally, generated with an un-optimized EPM, or generated using an EPM optimized by another procedure such as those described above (e.g., one not involving PLS). After receiving the training set, a PLS analysis is performed in operation 820 to generate an initial PLS model. The PLS model relates the coordinates of the etch profiles (received in operation 810) to the reflectance spectra (also received in operation 810). In particular embodiments, the PLS analysis generates a regression model which expresses the dependency of the etch profile coordinates at later etch times or even at the conclusion of the etch process on certain wavelengths of the reflectance spectra at particular times earlier in the etch process, as described above, as well as the statistical sensitivity of this dependence.

This initial PLS model may be accurate enough for some purposes, and if this is determined to be the case in operation 830, the optimization process concludes. However, if in operation 830 the PLS model is deemed to not be of sufficient accuracy, the process 801 continues to operation 840 where the current PLS model (as constructed in operation 820) is used to determine a (statistically significant) reduced dimensional subspace (RDS) along with statistical weights for defining an effective error metric (as described above). The new statistically-weighted spectral error metric is then used in operation 850 to optimize an EPM model according (for example) to the EPM optimization procedure described with respect to FIG. 6. Such a statistically-weighted error metric may be used (in the optimization, e.g., of FIG. 6) to act as an effectively gauge of the difference between EPM computed and corresponding measured reflectance spectra in a spectral subspace (of the full spectral space) deemed to be statistically significant by the PLS procedure.

This EPM optimization procedure may use the same spectral data as used in operation 820, or it may use different spectral data (but, again, it is optimized utilizing the new spectral error metric defined in operation 840). In any event, once the EPM is optimized (in operation 850) it may be used to generate a new (and perhaps very extensive) set of computed reflectance spectra. This is done by generating a set of computed etch profiles in in operation 860 and then in operation 865 using these computed etch profiles to generate a set of computed reflectance spectra (for example, by using RCWA as described above and indicated in the figure). These spectra may then be fed—as the spectral training set—back into operation 820 where a new PLS model is generated based on this new (perhaps quite extensive) training set. The statistical accuracy of the new PLS model is assessed in operation 830; and the cycle of operations (840, 850, 860, 865, 820, and 830) may be continued in repetition until, in one of the repetitions of operation 830, the PLS model is deemed to be of sufficient statistical accuracy.

It is noted that while this kind of PLS model is useful for optimizing an EPM model (via the identification of a "good" RDS) it is also independently useful for etch endpoint detection procedures, such as those described in a co-pending U.S. patent application Ser. No. 15/059,073 (hereby incorporated by reference in its entirety for all purposes). For instance, as described above, the PLS model may be viewed as a statistical determination of which spectral regions over the course of an etch process are more/most predictive of the final etch profile resulting from the etch process. As such, the construction of the PLS model is effectively a sensitivity analysis which identifies which spectral regions may be monitored over the course of an etch process to determine when the feature profile has been etched sufficiently (i.e., for endpoint detection). It is therefore also noted that the optimization of the EPM model through the statistical weighting of the optimization in favor of those spectral regions (as a function of etch time) which are important in the PLS model, in addition to potentially leading to a more efficient EPM optimization, has the benefit of enhancing the statistical accuracy of the PLS sensitivity analysis because the PLS model is thereby being constructed from etch profile data sets produced by an EPM model whose optimization was statistically weighted in favor of the same regions of the spectral space (over the etch process) which are deemed in important by the PLS analysis.

Capacitively Coupled Plasma (CCP) Reactors for Use in Etch Operations

Capacitively coupled plasma (CCP) reactors are described in U.S. Pat. No. 8,552,334, filed Feb. 9, 2009 as U.S. patent application Ser. No. 12/367,754, and titled "ADJUSTABLE GAP CAPACITIVELY COUPLED RF PLASMA REACTOR INCLUDING LATERAL BELLOWS AND NON-CONTACT PARTICLE SEAL," and in U.S. patent application Ser. No. 14/539,121, filed Nov. 12, 2014, and titled "ADJUSTMENT OF VUV EMISSION OF A PLASMA VIA COLLISIONAL RESONANT ENERGY TRANSFER TO AN ENERGY ABSORBER GAS," each of which is hereby incorporated by reference in its entirety for all purposes.

Figure 9A:
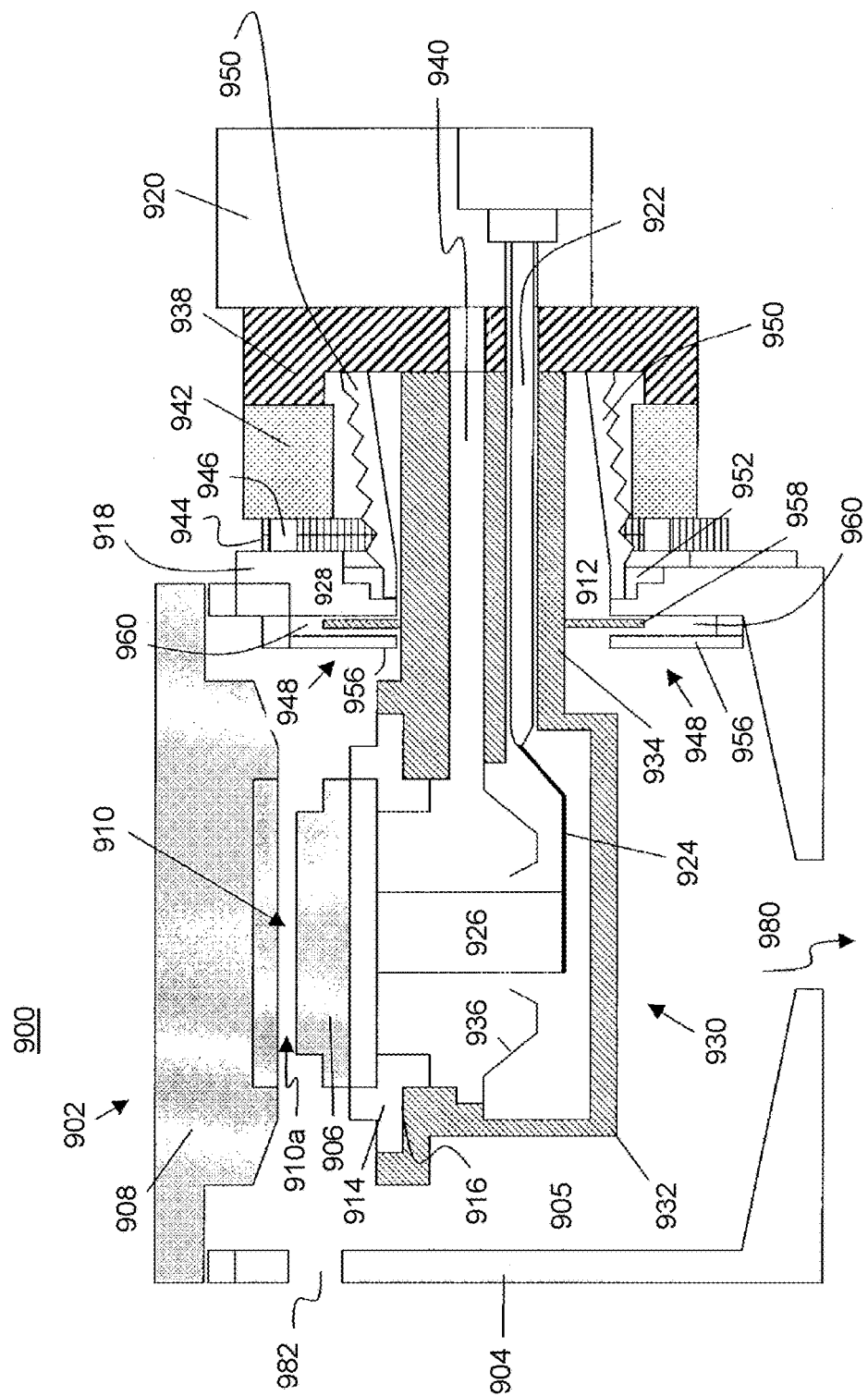
FIGS. 9A-9C illustrate an embodiment of an adjustable-gap capacitively-coupled (CCP) plasma reactor.
Figure 9B:
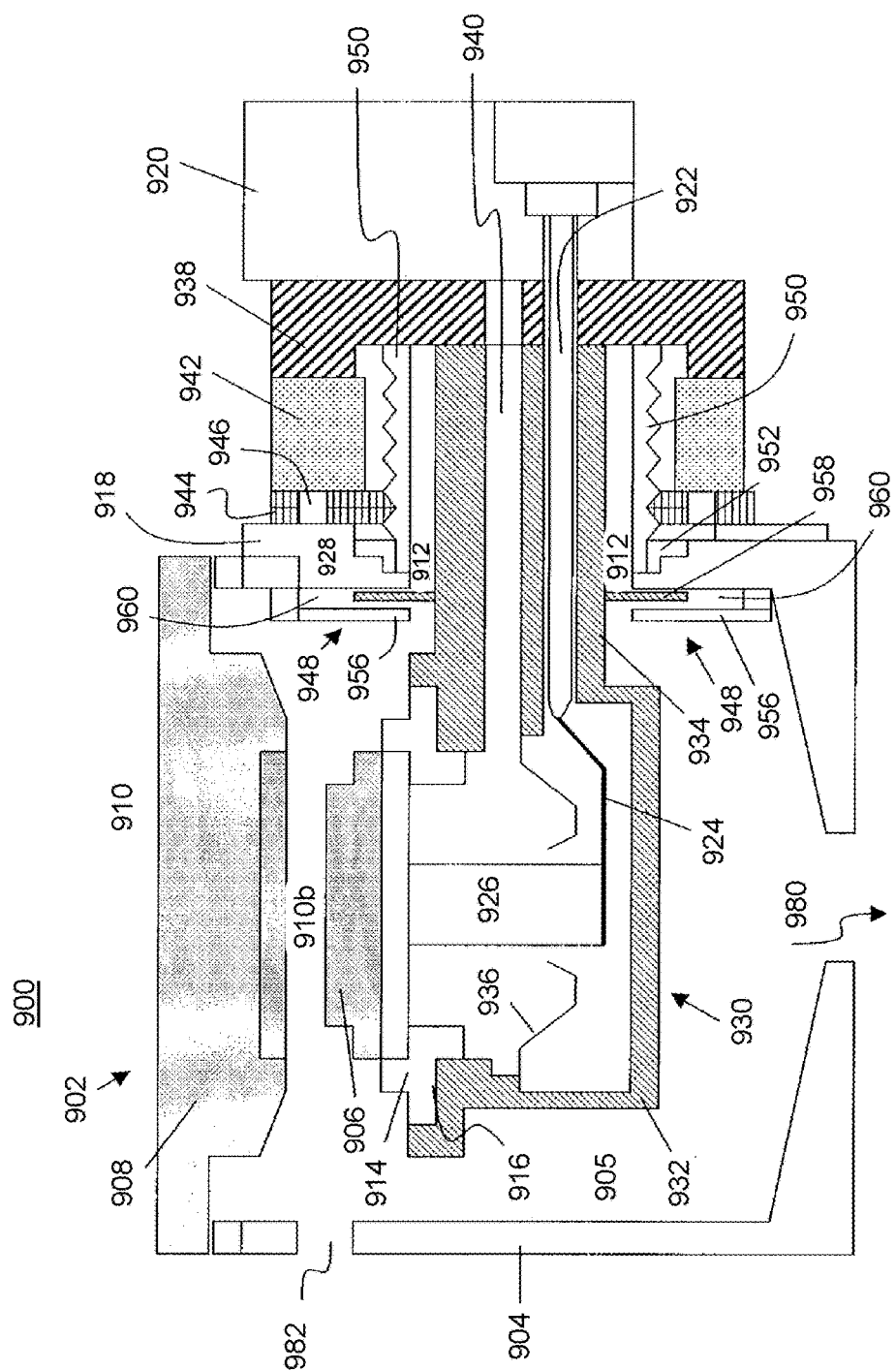
Figure 9C:
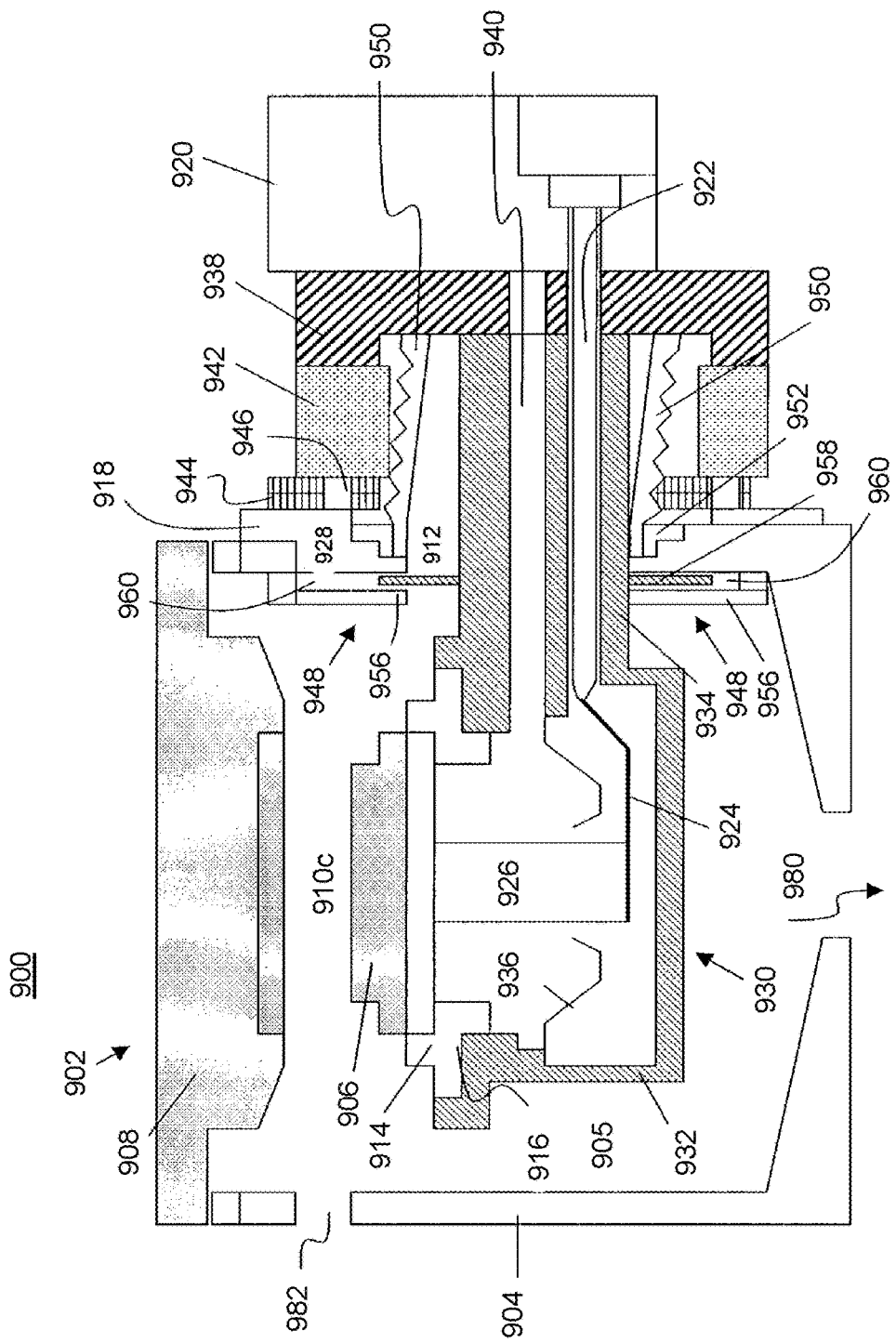

For instance, FIGS. 9A-9C illustrate an embodiment of an adjustable gap capacitively coupled confined RF plasma reactor 900. As depicted, a vacuum processing chamber 902 includes a chamber housing 904, surrounding an interior space housing a lower electrode 906. In an upper portion of the chamber 902 an upper electrode 908 is vertically spaced apart from the lower electrode 906. Planar surfaces of the upper and lower electrodes 908, 906 (configured to be used for plasma generation) are substantially parallel and orthogonal to the vertical direction between the electrodes. Preferably the upper and lower electrodes 908, 906 are circular and coaxial with respect to a vertical axis. A lower surface of the upper electrode 908 faces an upper surface of the lower electrode 906. The spaced apart facing electrode surfaces define an adjustable gap 910 there between. During plasma generation, the lower electrode 906 is supplied RF power by an RF power supply (match) 920. RF power is supplied to the lower electrode 906 though an RF supply conduit 922, an RF strap 924 and an RF power member 926. A grounding shield 936 may surround the RF power member 926 to provide a more uniform RF field to the lower electrode 906. As described in U.S. Pat. Pub. No. 2008/0171444 (which is hereby incorporated by reference in its entirety for all purposes), a wafer is inserted through wafer port 982 and supported in the gap 910 on the lower electrode 906 for processing, a process gas is supplied to the gap 910 and excited into plasma state by the RF power. The upper electrode 908 can be powered or grounded.

In the embodiment shown in FIGS. 9A-9C, the lower electrode 906 is supported on a lower electrode support plate 916. An insulator ring 914 interposed between the lower electrode 906 and the lower electrode support plate 916 insulates the lower electrode 906 from the support plate 916. An RF bias housing 930 supports the lower electrode 906 on an RF bias housing bowl 932. The bowl 932 is connected through an opening in a chamber wall plate 918 to a conduit support plate 938 by an arm 934 of the RF bias housing 930. In a preferred embodiment, the RF bias housing bowl 932 and RF bias housing arm 934 are integrally formed as one component, however, the arm 934 and bowl 932 can also be two separate components bolted or joined together.

The RF bias housing arm 934 includes one or more hollow passages for passing RF power and facilities, such as gas coolant, liquid coolant, RF energy, cables for lift pin control, electrical monitoring and actuating signals from outside the vacuum chamber 902 to inside the vacuum chamber 902 at a space on the backside of the lower electrode 906. The RF supply conduit 922 is insulated from the RF bias housing arm 934, the RF bias housing arm 934 providing a return path for RF power to the RF power supply 920. A facilities conduit 940 provides a passageway for facility components. Further details of the facility components are described in U.S. Pat. No. 5,948,704 and U.S. Pat. Pub. No. 2008/0171444 (both of which are hereby incorporated by reference in their entirety for all purposes) and are not shown here for simplicity of description. The gap 910 is preferably surrounded by a confinement ring assembly (not shown), details of which can be found in U.S. Pat. Pub. No. 2007/0284045 (which is hereby incorporated by reference in its entirety for all purposes).

The conduit support plate 938 is attached to an actuation mechanism 942. Details of an actuation mechanism are described in U.S. Pat. Pub. No. 2008/0171444 (which is hereby incorporated by reference in its entirety for all purposes). The actuation mechanism 942, such as a servo mechanical motor, stepper motor or the like is attached to a vertical linear bearing 944, for example, by a screw gear 946 such as a ball screw and motor for rotating the ball screw. During operation to adjust the size of the gap 910, the actuation mechanism 942 travels along the vertical linear bearing 944. FIG. 9A illustrates the arrangement when the actuation mechanism 942 is at a high position on the linear bearing 944 resulting in a small gap 910a. FIG. 9B illustrates the arrangement when the actuation mechanism 942 is at a mid-position on the linear bearing 944. As shown, the lower electrode 906, the RF bias housing 930, the conduit support plate 938, the RF power supply 920 have all moved lower with respect to the chamber housing 904 and the upper electrode 908, resulting in a medium size gap 910b.

FIG. 9C illustrates a large gap 910c when the actuation mechanism 942 is at a low position on the linear bearing. Preferably, the upper and lower electrodes 908, 906 remain co-axial during the gap adjustment and the facing surfaces of the upper and lower electrodes across the gap remain parallel.

This embodiment allows the gap 910 between the lower and upper electrodes 906, 908 in the CCP chamber 902 during multi-step etch processes to be adjusted, for example, in order to maintain uniform etch across a large diameter substrate such as 300 mm wafers or flat panel displays. In particular, this embodiment pertains to a mechanical arrangement to facilitate the linear motion necessary to provide the adjustable gap between lower and upper electrodes 906, 908.

FIG. 9A illustrates laterally deflected bellows 950 sealed at a proximate end to the conduit support plate 938 and at a distal end to a stepped flange 928 of chamber wall plate 918. The inner diameter of the stepped flange defines an opening 912 in the chamber wall plate 918 through which the RF bias housing arm 934 passes. The laterally deflected bellows 950 provides a vacuum seal while allowing vertical movement of the RF bias housing 930, conduit support plate 938 and actuation mechanism 942. The RF bias housing 930, conduit support plate 938 and actuation mechanism 942 can be referred to as a cantilever assembly. Preferably, the RF power supply 920 moves with the cantilever assembly and can be attached to the conduit support plate 938. FIG. 9B shows the bellows 950 in a neutral position when the cantilever assembly is at a mid-position. FIG. 9C shows the bellows 950 laterally deflected when the cantilever assembly is at a low position.

A labyrinth seal 948 provides a particle barrier between the bellows 950 and the interior of the plasma processing chamber housing 904. A fixed shield 956 is immovably attached to the inside inner wall of the chamber housing 904 at the chamber wall plate 918 so as to provide a labyrinth groove 960 (slot) in which a movable shield plate 958 moves vertically to accommodate vertical movement of the cantilever assembly. The outer portion of the movable shield plate 958 remains in the slot at all vertical positions of the lower electrode 906.

In the embodiment shown, the labyrinth seal 948 includes a fixed shield 956 attached to an inner surface of the chamber wall plate 918 at a periphery of the opening 912 in the chamber wall plate 918 defining a labyrinth groove 960. The movable shield plate 958 is attached and extends radially from the RF bias housing arm 934 where the arm 934 passes through the opening 912 in the chamber wall plate 918. The movable shield plate 958 extends into the labyrinth groove 960 while spaced apart from the fixed shield 956 by a first gap and spaced apart from the interior surface of the chamber wall plate 918 by a second gap allowing the cantilevered assembly to move vertically. The labyrinth seal 948 blocks migration of particles spalled from the bellows 950 from entering the vacuum chamber interior and blocks radicals from process gas plasma from migrating to the bellows 950 where the radicals can form deposits which are subsequently spalled.

FIG. 9A shows the movable shield plate 958 at a higher position in the labyrinth groove 960 above the RF bias housing arm 934 when the cantilevered assembly is in a high position (small gap 910a). FIG. 9C shows the movable shield plate 958 at a lower position in the labyrinth groove 960 above the RF bias housing arm 934 when the cantilevered assembly is in a low position (large gap 910c). FIG. 9B shows the movable shield plate 958 in a neutral or mid position within the labyrinth groove 960 when the cantilevered assembly is in a mid position (medium gap 910b). While the labyrinth seal 948 is shown as symmetrical about the RF bias housing arm 934, in other embodiments the labyrinth seal 948 may be asymmetrical about the RF bias arm 934.

Inductively Coupled Plasma Reactors for Use in Etch Operations

Inductively coupled plasma (ICP) reactors are described in US Pat. Pub. No. 2014/0170853, filed Dec. 10, 2013, and titled "IMAGE REVERSAL WITH AHM GAP FILL FOR MULTIPLE PATTERNING," and in U.S. patent application Ser. No. 14/539,121, filed Nov. 12, 2014, and titled "ADJUSTMENT OF VUV EMISSION OF A PLASMA VIA COLLISIONAL RESONANT ENERGY TRANSFER TO AN ENERGY ABSORBER GAS," each of which is hereby incorporated by reference in its entirety for all purposes.

Figure 10:
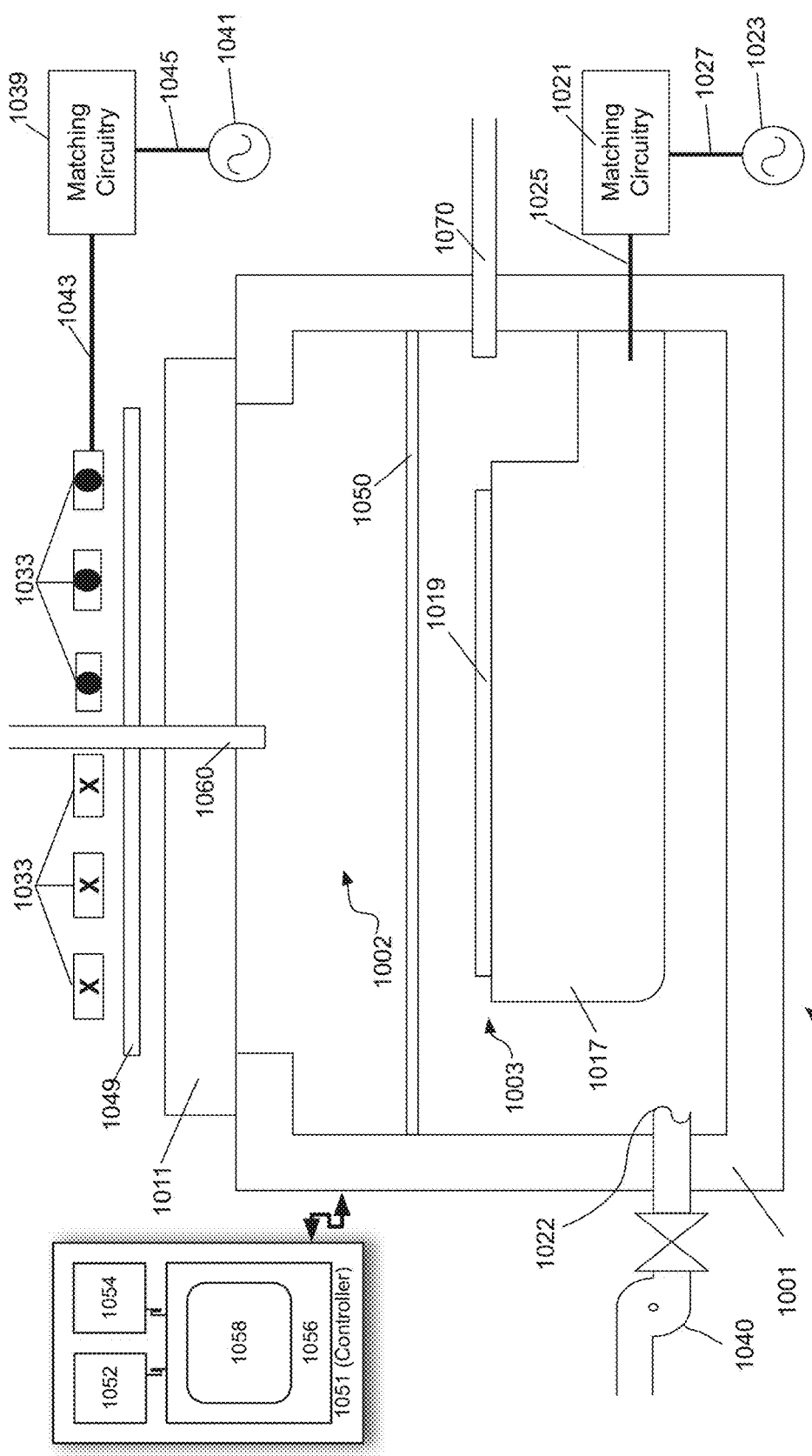
FIG. 10 illustrates an embodiment of an inductively-coupled plasma (ICP) reactor.

For instance, FIG. 10 schematically shows a cross-sectional view of an inductively coupled plasma etching apparatus 1000 appropriate for implementing certain embodiments herein, an example of which is a Kiyo™ reactor, produced by Lam Research Corp. of Fremont, Calif. The inductively coupled plasma etching apparatus 1000 includes an overall etching chamber structurally defined by chamber walls 1001 and a window 1011. The chamber walls 1001 may be fabricated from stainless steel or aluminum. The window 1011 may be fabricated from quartz or other dielectric material. An optional internal plasma grid 1050 divides the overall etching chamber into an upper sub-chamber 1002 and a lower sub-chamber 1003. In most embodiments, plasma grid 1050 may be removed, thereby utilizing a chamber space made of sub-chambers 1002 and 1003. A chuck 1017 is positioned within the lower sub-chamber 1003 near the bottom inner surface. The chuck 1017 is configured to receive and hold a semiconductor wafer 1019 upon which the etching process is performed. The chuck 1017 can be an electrostatic chuck for supporting the wafer 1019 when present. In some embodiments, an edge ring (not shown) surrounds chuck 1017, and has an upper surface that is approximately planar with a top surface of a wafer 1019, when present over chuck 1017. The chuck 1017 also includes electrostatic electrodes for chucking and dechucking the wafer. A filter and DC clamp power supply (not shown) may be provided for this purpose. Other control systems for lifting the wafer 1019 off the chuck 1017 can also be provided. The chuck 1017 can be electrically charged using an RF power supply 1023. The RF power supply 1023 is connected to matching circuitry 1021 through a connection 1027. The matching circuitry 1021 is connected to the chuck 1017 through a connection 1025. In this manner, the RF power supply 1023 is connected to the chuck 1017.

Elements for plasma generation include a coil 1033 is positioned above window 1011. The coil 1033 is fabricated from an electrically conductive material and includes at least one complete turn. The example of a coil 1033 shown in FIG. 10 includes three turns. The cross-sections of coil 1033 are shown with symbols, and coils having an "X" extend rotationally into the page, while coils having a "●" extend rotationally out of the page. Elements for plasma generation also include an RF power supply 1041 configured to supply RF power to the coil 1033. In general, the RF power supply 1041 is connected to matching circuitry 1039 through a connection 1045. The matching circuitry 1039 is connected to the coil 1033 through a connection 1043. In this manner, the RF power supply 1041 is connected to the coil 1033. An optional Faraday shield 1049 is positioned between the coil 1033 and the window 1011. The Faraday shield 1049 is maintained in a spaced apart relationship relative to the coil 1033. The Faraday shield 1049 is disposed immediately above the window 1011. The coil 1033, the Faraday shield 1049, and the window 1011 are each configured to be substantially parallel to one another. The Faraday shield may prevent metal or other species from depositing on the dielectric window of the plasma chamber.

Process gases (e.g. helium, neon, etchant, etc.) may be flowed into the processing chamber through one or more main gas flow inlets 1060 positioned in the upper chamber and/or through one or more side gas flow inlets 1070. Likewise, though not explicitly shown, similar gas flow inlets may be used to supply process gases to the capacitively coupled plasma processing chamber shown in FIGS. 9A-9C. A vacuum pump, e.g., a one or two stage mechanical dry pump and/or turbomolecular pump 1040, may be used to draw process gases out of the process chamber and to maintain a pressure within the process chamber. A valve-controlled conduit may be used to fluidically connect the vacuum pump to the processing chamber so as to selectively control application of the vacuum environment provided by the vacuum pump. This may be done employing a closed-loop-controlled flow restriction device, such as a throttle valve (not shown) or a pendulum valve (not shown), during operational plasma processing. Likewise, a vacuum pump and valve controlled fluidic connection to the capacitively coupled plasma processing chamber in FIGS. 9A-9C may also be employed.

During operation of the apparatus, one or more process gases may be supplied through the gas flow inlets 1060 and/or 1070. In certain embodiments, process gas may be supplied only through the main gas flow inlet 1060, or only through the side gas flow inlet 1070. In some cases, the gas flow inlets shown in the figure may be replaced more complex gas flow inlets, one or more showerheads, for example. The Faraday shield 1049 and/or optional grid 1050 may include internal channels and holes that allow delivery of process gases to the chamber. Either or both of Faraday shield 1049 and optional grid 1050 may serve as a showerhead for delivery of process gases.

Radio frequency power is supplied from the RF power supply 1041 to the coil 1033 to cause an RF current to flow through the coil 1033. The RF current flowing through the coil 1033 generates an electromagnetic field about the coil 1033. The electromagnetic field generates an inductive current within the upper sub-chamber 1002. The physical and chemical interactions of various generated ions and radicals with the wafer 1019 selectively etch features of the wafer.

If the plasma grid is used such that there is both an upper sub-chamber 1002 and a lower sub-chamber 1003, the inductive current acts on the gas present in the upper sub-chamber 1002 to generate an electron-ion plasma in the upper sub-chamber 1002. The optional internal plasma grid 1050 limits the amount of hot electrons in the lower sub-chamber 1003. In some embodiments, the apparatus is designed and operated such that the plasma present in the lower sub-chamber 1003 is an ion-ion plasma.

Both the upper electron-ion plasma and the lower ion-ion plasma may contain positive and negative ions, through the ion-ion plasma will have a greater ratio of negative ions to positive ions. Volatile etching byproducts may be removed from the lower-subchamber 1003 through port 1022.

The chuck 1017 disclosed herein may operate at elevated temperatures ranging between about 10° C. and about 250° C. The temperature will depend on the etching process operation and specific recipe. In some embodiments, the chamber 1001 may also operate at pressures in the range of between about 1 mTorr and about 95 mTorr. In certain embodiments, the pressure may be higher as disclosed above.

The chamber 1001 may be coupled to facilities (not shown) when installed in a clean room or a fabrication facility. Facilities include plumbing that provide processing gases, vacuum, temperature control, and environmental particle control. These facilities are coupled to the chamber 1001, when installed in the target fabrication facility. Additionally, the chamber 1001 may be coupled to a transfer chamber that allows robotics to transfer semiconductor wafers into and out of the chamber 1001 using typical automation.

Also shown in FIG. 10 is system controller 1051. As described further below, such a system controller 1051 may control some or all of the operations of an etcher apparatus, including adjustment of the etcher's operation in response to the generation of a computed etch profile using an optimized EMP as described herein.

System Controllers

A system controller may be used to control etching operations (or other processing operations) in any of the above described processing apparatuses, such as the CCP etcher apparatuses shown in FIGS. 9A-9C, and/or the ICP etcher apparatus shown in FIG. 10. In particular, the system controller may implement an optimized EPM as described above and adjust operation of an etcher apparatus in response to computed etch profiles generated using the optimized EPM (as described above).

An example of a system controller in communication with an etcher apparatus is schematically illustrated in FIG. 10. As shown in FIG. 10, system controller 1051 includes one or more memory devices 1056, one or more mass storage devices 1054, and one or more processors 1052. Processor 1052 may include one or more CPUs, ASICs, general-purpose computer(s) and/or specific purpose computer(s), one or more analog and/or digital input/output connection(s), one or more stepper motor controller board(s), etc.

In some embodiments, a system controller (e.g., 1050 in FIG. 10) controls some or all of the operations of a process tool (e.g., etcher apparatus 1000 in FIG. 10) including the operations of its individual process stations. Machine-readable system control instructions 1058 may be provided for implementing/performing the film deposition and/or etch processes described herein. The instructions may be provided on machine-readable, non-transitory media which may be coupled to and/or read by the system controller. The instructions may be executed on processor 1052—the system control instructions, in some embodiments, loaded into memory device 1056 from mass storage device 1054. System control instructions may include instructions for controlling the timing, mixture of gaseous and liquid reactants, chamber and/or station pressures, chamber and/or station temperatures, wafer temperatures, target power levels, RF power levels (e.g., DC power levels, RF bias power levels), RF exposure times, substrate pedestal, chuck, and/or susceptor positions, and other parameters of a particular process performed by a process tool.

Semiconductor substrate processing operations may employ various types of processes including, but not limited to, processes related to the etching of film on substrates (such as by atomic layer etch (ALE) operations involving plasma-activation of surface adsorbed etchants, see, e.g., U.S. patent application Ser. No. 14/539,121, filed Nov. 12, 2014 (U.S. Publication No. 20160135274), titled "ADJUSTMENT OF VUV EMISSION OF A PLASMA VIA COLLISIONAL RESONANT ENERGY TRANSFER TO AN ENERGY ABSORBER GAS," which is hereby incorporated by reference in its entirety for all purposes), deposition processes (such as atomic layer deposition (ALD), by plasma-activation of surface adsorbed film precursors), as well as other types of substrate processing operations.

Thus, for example, with respect to a processing apparatus for performing plasma-based etch processes, the machine-readable instructions executed by a system controller may include instructions for generating a computed etch profile from an optimized EPM and adjusting operation of the plasma generator in response to the computed etch profile.

System control instructions 1058 may be configured in any suitable way. For example, various process tool component subroutines or control objects may be written to control operation of the process tool components necessary to carry out various process tool processes. System control instructions may be coded in any suitable computer readable programming language. In some embodiments, system control instructions are implemented in software, in other embodiments, the instructions may be implemented in hardware—for example, hard-coded as logic in an ASIC (application specific integrated circuit), or, in other embodiments, implemented as a combination of software and hardware.

In some embodiments, system control software 1058 may include input/output control (IOC) sequencing instructions for controlling the various parameters described above. For example, each phase of a deposition and/or etch process or processes may include one or more instructions for execution by the system controller. The instructions for setting process conditions for a film deposition and/or etch process phase, for example, may be included in a corresponding deposition and/or etch recipe phase. In some embodiments, the recipe phases may be sequentially arranged, so that all instructions for a process phase are executed concurrently with that process phase.

Other computer-readable instructions and/or programs stored on mass storage device 1054 and/or memory device 1056 associated with system controller 1051 may be employed in some embodiments. Examples of programs or sections of programs include a substrate positioning program, a process gas control program, a pressure control program, a heater control program, and a plasma control program.

A substrate positioning program may include instructions for process tool components that are used to load the substrate onto pedestal and to control the spacing between the substrate and other parts of process tool. The positioning program may include instructions for appropriately moving substrates in and out of the reaction chamber as necessary to deposit and/or etch film on the substrates.

A process gas control program may include instructions for controlling gas composition and flow rates and optionally for flowing gas into the volumes surrounding one or more process stations prior to deposition and/or etch in order to stabilize the pressure in these volumes. In some embodiments, the process gas control program may include instructions for introducing certain gases into the volume(s) surrounding the one or more process stations within a processing chamber during film deposition and/or etching operations on substrates. The process gas control program may also include instructions to deliver these gases at the same rates, for the same durations, or at different rates and/or for different durations depending on the composition of the film being deposited and/or the nature of the etching process involved. The process gas control program may also include instructions for atomizing/vaporizing a liquid reactant in the presence of helium or some other carrier gas in a heated injection module.

A pressure control program may include instructions for controlling the pressure in the process station by regulating, for example, a throttle valve in the exhaust system of the process station, a gas flow into the process station, etc. The pressure control program may include instructions for maintaining the same or different pressures during deposition of the various film types on the substrates and/or etching of the substrates.

A heater control program may include instructions for controlling the current to a heating unit that is used to heat the substrates. Alternatively or in addition, the heater control program may control delivery of a heat transfer gas (such as helium) to the substrate. The heater control program may include instructions for maintaining the same or different temperatures in the reaction chamber and/or volumes surrounding the process stations during deposition of the various film types on the substrates and/or etching of the substrates.

A plasma control program may include instructions for setting RF power levels, frequencies, and exposure times in one or more process stations in accordance with the embodiments herein. In some embodiments, the plasma control program may include instructions for using the same or different RF power levels and/or frequencies and/or exposure times during film deposition on and/or etching of the substrates.

In some embodiments, there may be a user interface associated with the system controller. The user interface may include a display screen, graphical software displays of the apparatus and/or process conditions, and user input devices such as pointing devices, keyboards, touch screens, microphones, etc.

In some embodiments, parameters adjusted by system controller may relate to process conditions. Non-limiting examples include process gas compositions and flow rates, temperatures (e.g., substrate holder and showerhead temperatures), pressures, plasma conditions (such as RF bias power levels and exposure times), etc. These parameters may be provided to the user in the form of a recipe, which may be entered utilizing the user interface.

Signals for monitoring the processes may be provided by analog and/or digital input connections of the system controller from various process tool sensors. The signals for controlling the processes may be output on the analog and/or digital output connections of the process tool. Non-limiting examples of process tool sensors that may be monitored include mass flow controllers (MFCs), pressure sensors (such as manometers), temperature sensors such as thermocouples, etc. Appropriately programmed feedback and control algorithms may be used with data from these sensors to maintain process conditions.

The various apparatuses and methods described above may be used in conjunction with lithographic patterning tools and/or processes, for example, for the fabrication or manufacture of semiconductor devices, displays, LEDs, photovoltaic panels and the like. Typically, though not necessarily, such tools will be used or processes conducted together and/or contemporaneously in a common fabrication facility.

In some implementations, a controller is part of a system, which may be part of the above-described examples. Such systems can comprise semiconductor processing equipment, including a processing tool or tools, chamber or chambers, a platform or platforms for processing, and/or specific processing components (a wafer pedestal, a gas flow system, etc.). These systems may be integrated with electronics for controlling their operation before, during, and after processing of a semiconductor wafer or substrate. The electronics may be referred to as the "controller," which may control various components or subparts of the system or systems. The controller, depending on the processing requirements and/or the type of system, may be programmed to control any of the processes disclosed herein, including the delivery of processing gases, temperature settings (e.g., heating and/or cooling), pressure settings, vacuum settings, power settings, radio frequency (RF) generator settings, RF matching circuit settings, frequency settings, flow rate settings, fluid delivery settings, positional and operation settings, wafer transfers into and out of a tool and other transfer tools and/or load locks connected to or interfaced with a specific system.

Broadly speaking, the controller may be defined as electronics having various integrated circuits, logic, memory, and/or software that receive instructions, issue instructions, control operation, enable cleaning operations, enable endpoint measurements, and the like. The integrated circuits may include chips in the form of firmware that store program instructions, digital signal processors (DSPs), chips defined as application specific integrated circuits (ASICs), and/or one or more microprocessors, or microcontrollers that execute program instructions (e.g., software). Program instructions may be instructions communicated to the controller in the form of various individual settings (or program files), defining operational parameters for carrying out a particular process on or for a semiconductor wafer or to a system. The operational parameters may, in some embodiments, be part of a recipe defined by process engineers to accomplish one or more processing steps during the fabrication of one or more layers, materials, metals, oxides, silicon, silicon dioxide, surfaces, circuits, and/or dies of a wafer.

The controller, in some implementations, may be a part of or coupled to a computer that is integrated with, coupled to the system, otherwise networked to the system, or a combination thereof. For example, the controller may be in the "cloud" or all or a part of a fab host computer system, which can allow for remote access of the wafer processing. The computer may enable remote access to the system to monitor current progress of fabrication operations, examine a history of past fabrication operations, examine trends or performance metrics from a plurality of fabrication operations, to change parameters of current processing, to set processing steps to follow a current processing, or to start a new process. In some examples, a remote computer (e.g. a server) can provide process recipes to a system over a network, which may include a local network or the Internet. The remote computer may include a user interface that enables entry or programming of parameters and/or settings, which are then communicated to the system from the remote computer. In some examples, the controller receives instructions in the form of data, which specify parameters for each of the processing steps to be performed during one or more operations. It should be understood that the parameters may be specific to the type of process to be performed and the type of tool that the controller is configured to interface with or control. Thus as described above, the controller may be distributed, such as by comprising one or more discrete controllers that are networked together and working towards a common purpose, such as the processes and controls described herein. An example of a distributed controller for such purposes would be one or more integrated circuits on a chamber in communication with one or more integrated circuits located remotely (such as at the platform level or as part of a remote computer) that combine to control a process on the chamber.

Without limitation, example systems may include a plasma etch chamber or module (employing inductively or capacitively coupled plasmas), a deposition chamber or module, a spin-rinse chamber or module, a metal plating chamber or module, a clean chamber or module, a bevel edge etch chamber or module, a physical vapor deposition (PVD) chamber or module, a chemical vapor deposition (CVD) chamber or module, an atomic layer deposition (ALD) chamber or module, an atomic layer etch (ALE) chamber or module, an ion implantation chamber or module, a track chamber or module, and any other semiconductor processing systems that may be associated or used in the fabrication and/or manufacturing of semiconductor wafers.

As noted above, depending on the process step or steps to be performed by the tool, the controller might communicate with one or more of other tool circuits or modules, other tool components, cluster tools, other tool interfaces, adjacent tools, neighboring tools, tools located throughout a factory, a main computer, another controller, or tools used in material transport that bring containers of wafers to and from tool locations and/or load ports in a semiconductor manufacturing factory.

Other Embodiments

Although the foregoing disclosed techniques, operations, processes, methods, systems, apparatuses, tools, films, chemistries, and compositions have been described in detail within the context of specific embodiments for the purpose of promoting clarity and understanding, it will be apparent to one of ordinary skill in the art that there are many alternative ways of implementing the foregoing embodiments which are within the spirit and scope of this disclosure. Accordingly, the embodiments described herein are to be viewed as illustrative of the disclosed inventive concepts rather than restrictively, and are not to be used as an impermissible basis for unduly limiting the scope of any claims eventually directed to the subject matter of this disclosure.

What is claimed is:

1. A computer implemented method of optimizing a computer model which relates etch profiles of features on semiconductor substrates to a set of independent input parameters, the method comprising:
    (a) identifying values for one or more model parameters to be optimized, wherein the model parameters are used in executing the computer model;
    (b) receiving experimental reflectance spectra generated from optical measurements of one or more semiconductor substrates etched using an experimental etch process performed using values of the set of independent input parameters;
    (c) generating, by using a computer processor, computed reflectance spectra by executing the computer model using the values for the set of independent input parameters specified in (b) and values of the model parameters identified in (a); and
    (d) modifying, by using a computer processor, the values of the one or more model parameters identified in (a) and repeating (c) with the modified values of the one or more model parameters so as to reduce a metric indicative of the differences between the experimental reflectance spectra received in (b) and corresponding computed reflectance spectra generated in (c) with respect to the values of the set of independent input parameters, thereby producing modified values for the one or more model parameters for use in the computer model which relates etch profiles of features on semiconductor substrates to the set of independent input parameters.

2. The method of claim 1, wherein at least some of the computed reflectance spectra are generated by a process comprising:
    (i) generating a computed etch profile represented by a series of etch profile coordinates using the model;
    (ii) from the computed etch profile generated in (i), generating a computed reflectance spectrum by simulating the reflection of electromagnetic radiation off of said computed etch profile.

3. The method of claim 1, wherein:
    the experimental reflectance spectra received in (b) comprise reflectance spectra corresponding to a sequence of etch times representing different durations of etch processes; and
    the computed reflectance spectra generated in (c) comprise reflectance spectra computed from the model so as to correspond to the sequence of etch times in (b).

4. The method of claim 3, wherein the experimental reflectance spectra are received in (b) from optical measurements taken during ongoing etch processes at the sequence of etch times.

5. The method of claim 4, wherein consecutive etch times over at least a portion of the sequence of etch times are separated by 0.01-1 second.

6. The method of claim 4, wherein at least some of the experimental reflectance spectra received in (b) were adjusted based on comparisons with optical measurements taken with respect to, and after the conclusion of, substrate etch processes of various durations.

7. The method of claim 6, wherein the optical measurements corresponding to the concluded etch processes of various duration were taken after the corresponding etched substrates were removed from the processing chambers in which they were etched.

8. The method of claim 1, further comprising repeating (d).

9. The method of claim 8, further comprising further repeating (d) until a substantially local minimum in error with respect to the one or more model parameters is obtained.

10. The method of claim 1, wherein the computer model calculates local etch rates at a grid of points representing the etch profile of the feature on the semiconductor substrate as a function of time.

11. The method of claim 10, wherein the one or more model parameters include reaction rate constants, reactant and product sticking coefficients, and/or reactant and product diffusion constants.

12. The method of claim 1, further comprising identifying the set of independent input parameters by performing PCA.

13. The method of claim 12, wherein the PCA is performed with respect to concatenated vectors of independent input parameters and corresponding measured etch profiles.

14. The method of claim 1, further comprising etching a semiconductor substrate using or adjusting a set of etch conditions determined using the computer model with the modified values of the one or more model parameters.

15. An optimized computer model comprising a non-transitory computer readable medium on which is provided computer executable instructions encoding a computer model, which relates etch profiles of features on semiconductor substrates to the set of independent input parameters, configured with the modified values for the one or more model parameters, wherein the computer model was optimized by operations (a)-(d) of claim 1.

16. A computer implemented method of approximately determining the profile of a feature on a semiconductor substrate after the feature has been etched by an etch process, the method comprising:
    specifying test values for the set of independent input parameters corresponding to the etch process; and generating, by a computer processor, an etch profile using the optimized computer model of claim 15 with the specified test values for the set of independent input parameters.

17. A method of determining a set of values for a set of independent input parameters for an etch process which will approximately yield a desired etch profile of a feature on a semiconductor substrate after the feature is etched by said etch process, the method comprising:
(a) specifying test values for the set of independent input parameters corresponding to the etch process;
(b) generating a computed etch profile using the optimized computer model of claim 15 with the specified set of test values for the independent input parameters;
(c) computing a metric indicative of the difference between the desired etch profile and the computed etch profile; and
(d) modifying one or more values for the set of independent input parameters specified in (a) so as to reduce the difference between desired and computed etch profiles as ascertained by repeating (b)-(c).

18. The method of claim 17, further comprising:
(e) repeating (d) until a substantially local minimum in error with respect to the values for the set of independent input parameters selected in (d) is obtained.

19. A system for processing semiconductor substrates, the system comprising:
an etcher apparatus for etching semiconductor substrates whose operation is adjusted by a set of independent input parameters; and
a controller for controlling the operation of the etcher apparatus, the controller comprising a processor and a memory;
wherein:
the memory stores an etched feature profile model optimized by operations (a)-(d) of claim 1; and
the processor is configured to use the etched feature profile model stored in the memory to compute an etched feature profile from a set of values for the set of independent input parameters.

20. The system of claim 19, wherein the controller adjusts the operation of the etcher apparatus by varying one or more values of the set of independent input parameters in response to the computed etched feature profile.

21. The system of claim 20, wherein the set of independent input parameters whose values are varied in response to the computed etched feature profile include one or more parameters selected from: RF plasma frequency and RF plasma power level.

22. The system of claim 19, wherein the etcher apparatus comprises:
a processing chamber;
a substrate holder for holding a substrate within the processing chamber;
a plasma generator for generating a plasma within the processing chamber, the plasma generator comprising an RF power supply;
one or more valve-controlled process gas inlets for flowing one or more process gases into the processing chamber; and
one or more gas outlets fluidically connected to one or more vacuum pumps for evacuating gases from the processing chamber.

23. The system of claim 22, wherein the controller is configured to adjust the frequency and/or the power level of the RF power supply to modify characteristics of the plasma in the processing chamber in response to the computed etched feature profile.

24. The system of claim 22, wherein the controller is configured to operate the one or more valve-controlled process gas inlets to adjust the flow rates of one or more process gases into the processing chamber in response to the computed etched feature profile.

25. The system of claim 22, wherein the controller is configured to adjust a temperature and/or a pressure within the processing chamber in response to the computed etched feature profile.

26. The method of claim 1, wherein the computer model enables development of etch process parameters, wherein the computer model is optimized with the modified values, as produced in (d), for the one or more model parameters.

27. The method of claim 1, wherein the computer model enables development of lithography masks for etch processes, wherein the computer model is optimized with the modified values, as produced in (d), for the one or more model parameters.

28. The optimized computer model of claim 15, wherein the computer executable instructions further comprise instructions for developing lithography masks for etch processes.

29. The optimized computer model of claim 15, wherein the computer executable instructions further comprise instructions for developing etch process parameters.

* * * * *